United States Patent
Currie et al.

(10) Patent No.: US 9,303,066 B2
(45) Date of Patent: Apr. 5, 2016

(54) TREATMENTS FOR GASTROINTESTINAL DISORDERS

(75) Inventors: Mark G. Currie, Sterling, MA (US); Daniel P. Zimmer, Somerville, MA (US); Marco Kessler, Danvers, MA (US)

(73) Assignee: Ironwood Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/116,891

(22) PCT Filed: May 11, 2012

(86) PCT No.: PCT/US2012/037663
§ 371 (c)(1),
(2), (4) Date: Jul. 2, 2014

(87) PCT Pub. No.: WO2012/155114
PCT Pub. Date: Nov. 15, 2012

(65) Prior Publication Data
US 2014/0323397 A1    Oct. 30, 2014

Related U.S. Application Data

(60) Provisional application No. 61/485,060, filed on May 11, 2011.

(51) Int. Cl.
*C07K 7/08* (2006.01)
*A61K 38/04* (2006.01)

(52) U.S. Cl.
CPC .. *C07K 7/08* (2013.01); *A61K 38/04* (2013.01)

(58) Field of Classification Search
CPC ... A61K 2300/00; A61K 38/04; A61K 38/10; A61K 38/00; A61K 38/12; C07K 7/08; C07K 14/4705; C07K 17/195
See application file for complete search history.

(56) References Cited

U.S. PATENT DOCUMENTS

| | | | |
|---|---|---|---|
| 5,518,888 A | 5/1996 | Waldman | |
| 5,601,990 A | 2/1997 | Waldman | |
| 5,879,656 A | 3/1999 | Waldman | |
| 5,962,220 A | 10/1999 | Waldman | |
| 6,060,037 A | 5/2000 | Waldman | |
| 7,304,036 B2 | 12/2007 | Currie et al. | |
| 7,371,727 B2 | 5/2008 | Currie et al. | |
| 7,494,979 B2 | 2/2009 | Currie et al. | |
| 7,704,947 B2 | 4/2010 | Currie et al. | |
| 7,745,409 B2 | 6/2010 | Currie et al. | |
| 7,772,188 B2 | 8/2010 | Currie et al. | |
| 7,910,546 B2 | 3/2011 | Currie et al. | |
| 8,080,526 B2 | 12/2011 | Currie et al. | |
| 8,101,579 B2 | 1/2012 | Currie et al. | |
| 8,110,553 B2 | 2/2012 | Currie et al. | |
| 8,507,447 B2 | 8/2013 | Currie et al. | |
| 8,735,360 B2 | 5/2014 | Currie et al. | |
| 8,946,118 B2 | 2/2015 | Currie et al. | |
| 2009/0192083 A1 | 7/2009 | Currie et al. | |
| 2009/0253634 A1 | 10/2009 | Currie et al. | |
| 2010/0048489 A1 | 2/2010 | Fretzen et al. | |
| 2012/0039949 A1 | 2/2012 | Fretzen et al. | |
| 2013/0085107 A1 | 4/2013 | Currie et al. | |
| 2014/0342996 A1 | 11/2014 | Currie et al. | |
| 2014/0348942 A1 | 11/2014 | Currie et al. | |
| 2015/0030697 A1 | 1/2015 | Currie et al. | |

FOREIGN PATENT DOCUMENTS

| | | | |
|---|---|---|---|
| WO | WO0180871 | 11/2001 | |
| WO | WO2005087797 | 9/2005 | |
| WO | WO2006001931 | 1/2006 | |
| WO | WO2007022531 | 2/2007 | |
| WO | WO 2008/151257 A2 * | 12/2008 | ............ C07K 7/08 |
| WO | WO2008151257 | 12/2008 | |
| WO | WO2010065524 | 6/2010 | |
| WO | WO2011156453 | 12/2011 | |
| WO | WO2012155108 | 11/2012 | |

OTHER PUBLICATIONS

Sindic et al., "Guanylin and uroguanylin regulate electrolyte transport in isolated human cortical collecting ducts." Kidney Int. 67:1420-1427, 2005.

* cited by examiner

*Primary Examiner* — Karlheinz R Skowronek
*Assistant Examiner* — Jia-Hai Lee
(74) *Attorney, Agent, or Firm* — Honigman Miller Schwartz and Cohn LLP; Kelly T. Murphy; Jonathan P. O'Brien

(57) ABSTRACT

The present invention provides new uroguanylin derivatives that are useful for the treatment of gastrointestinal disorders. The present invention also provides compositions and methods of treating gastrointestinal disorders and pharmaceutical compositions for accomplishing the same. In some embodiments, these pharmaceutical compositions include oral dosage forms.

21 Claims, No Drawings

SEQUENCE LISTING

<160> NUMBER OF SEQ ID NOS: 33

<210> SEQ ID NO 1
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa1 is Ser, Asn, Tyr, Ala, Gln, Pro, Lys, Gly
      or Thr, or is missing
<220> FEATURE:
<221> NAME/KEY: VARIANT
<222> LOCATION: (2)..(2)
<223> OTHER INFORMATION: Xaa2 is His, Asp, Glu, Ala, Ser, Asn, Gly, or
      is missing
<220> FEATURE:
<221> NAME/KEY: VARIANT
<222> LOCATION: (3)..(3)
<223> OTHER INFORMATION: Xaa3 is Thr, Asp, Ser, Glu, Pro, Val or Leu
<220> FEATURE:
<221> NAME/KEY: MOD_RES
<222> LOCATION: (5)..(5)
<223> OTHER INFORMATION: Xaa is P-Ser, P-Thr, P-homo-Ser,
      4-hydroxyvaline phosphate, P-homo-Thr, P-Cys or P-Tyr
<220> FEATURE:
<221> NAME/KEY: VARIANT
<222> LOCATION: (6)..(6)
<223> OTHER INFORMATION: Xaa6 is Ile, Trp or Leu
<220> FEATURE:
<221> NAME/KEY: VARIANT
<222> LOCATION: (7)..(7)
<223> OTHER INFORMATION: Xaa7 is Cys, Ser, or Tyr
<220> FEATURE:
<221> NAME/KEY: VARIANT
<222> LOCATION: (8)..(8)
<223> OTHER INFORMATION: Xaa8 is Ala, Val, Thr, Ile, Met or is missing
<220> FEATURE:
<221> NAME/KEY: VARIANT
<222> LOCATION: (9)..(9)
<223> OTHER INFORMATION: Xaa9 is a) any amino acid, b) Phe, Tyr, Asn,
      Trp, c) an amino acid other than Phe, Trp, or Tyr, d) non-aromatic
      amino acid or e) is missing
<220> FEATURE:
<221> NAME/KEY: VARIANT
<222> LOCATION: (10)..(10)
<223> OTHER INFORMATION: Xaa10 is Ala, Val, Met, Thr or Ile
<220> FEATURE:
<221> NAME/KEY: VARIANT
<222> LOCATION: (11)..(11)
<223> OTHER INFORMATION: Xaa11 is Ala or Val
<220> FEATURE:
<221> NAME/KEY: VARIANT
<222> LOCATION: (13)..(13)
<223> OTHER INFORMATION: Xaa11 is Ala or Thr
<220> FEATURE:
<221> NAME/KEY: VARIANT
<222> LOCATION: (14)..(14)
<223> OTHER INFORMATION: Xaa14 Gly, Ala or Ser
<220> FEATURE:
<221> NAME/KEY: VARIANT
<222> LOCATION: (15)..(15)
<223> OTHER INFORMATION: Xaa15 is Cys, Tyr or is missing
<220> FEATURE:
<221> NAME/KEY: VARIANT
<222> LOCATION: (16)..(16)
<223> OTHER INFORMATION: Xaa16 is Trp, Tyr, Phe, Lys, Arg, His, Leu, Ser
      or is missing

<400> SEQUENCE: 1

Xaa Xaa Xaa Cys Xaa Xaa Xaa Xaa Xaa Xaa Xaa Cys Xaa Xaa Xaa Xaa
1               5                   10                  15

<210> SEQ ID NO 2

-continued

```
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa1 is Ser, Asn, Tyr, Ala, Gln, Pro, Lys, Gly,
      or Thr or is missing
<220> FEATURE:
<221> NAME/KEY: VARIANT
<222> LOCATION: (2)..(2)
<223> OTHER INFORMATION: Xaa2 is His, Asp, Glu, Ala, Ser, Asn, Gly, Pro
      or is missing
<220> FEATURE:
<221> NAME/KEY: VARIANT
<222> LOCATION: (3)..(3)
<223> OTHER INFORMATION: Xaa3 is Thr, Asp, Ser, Glu, Pro, Val or Leu
<220> FEATURE:
<221> NAME/KEY: MOD_RES
<222> LOCATION: (5)..(5)
<223> OTHER INFORMATION: Xaa5 is P-Ser, P-Thr, P-homo-Ser,
      4-hydroxyvaline phosphate, P-homo-Thr, P-Cys or P-Tyr
<220> FEATURE:
<221> NAME/KEY: VARIANT
<222> LOCATION: (6)..(6)
<223> OTHER INFORMATION: Xaa6 is Ile, Trp or Leu
<220> FEATURE:
<221> NAME/KEY: VARIANT
<222> LOCATION: (7)..(7)
<223> OTHER INFORMATION: Xaa7 is Cys, Ser, or Tyr
<220> FEATURE:
<221> NAME/KEY: VARIANT
<222> LOCATION: (8)..(8)
<223> OTHER INFORMATION: Xaa8 is Ala, Val, Thr, Ile, Met or is missing
<220> FEATURE:
<221> NAME/KEY: VARIANT
<222> LOCATION: (9)..(9)
<223> OTHER INFORMATION: Xaa9 is Phe, Tyr, Asn, Trp, an amino acid other
      than Phe, Trp, or Tyr, is a non-aromatic amino acid or is missing
<220> FEATURE:
<221> NAME/KEY: VARIANT
<222> LOCATION: (10)..(10)
<223> OTHER INFORMATION: Xaa10 is Ala, Val, Met, Thr, or Ile
<220> FEATURE:
<221> NAME/KEY: VARIANT
<222> LOCATION: (11)..(11)
<223> OTHER INFORMATION: Xaa11 is Ala or Val
<220> FEATURE:
<221> NAME/KEY: VARIANT
<222> LOCATION: (13)..(13)
<223> OTHER INFORMATION: Xaa13 is Ala or Thr
<220> FEATURE:
<221> NAME/KEY: VARIANT
<222> LOCATION: (14)..(14)
<223> OTHER INFORMATION: Xaa14 is Gly, Ala or Ser
<220> FEATURE:
<221> NAME/KEY: VARIANT
<222> LOCATION: (15)..(15)
<223> OTHER INFORMATION: Xaa15 is Cys, Tyr or is missing
<220> FEATURE:
<221> NAME/KEY: VARIANT
<222> LOCATION: (16)..(16)
<223> OTHER INFORMATION: Xaa16 is Trp, Tyr, Phe, Lys, Arg, His, Leu, Ser
      or is missing

<400> SEQUENCE: 2

Xaa Xaa Xaa Cys Xaa Xaa Xaa Xaa Xaa Xaa Xaa Cys Xaa Xaa Xaa Xaa
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetically generated peptide
```

```
<220> FEATURE:
<221> NAME/KEY: VARIANT
<222> LOCATION: (1)..(1)
<223> OTHER INFORMATION: Xaa1 is Asn, any amino acid or is missing
<220> FEATURE:
<221> NAME/KEY: VARIANT
<222> LOCATION: (2)..(2)
<223> OTHER INFORMATION: Xaa2 is Asp, Glu, any amino acid or is missing
<220> FEATURE:
<221> NAME/KEY: VARIANT
<222> LOCATION: (3)..(3)
<223> OTHER INFORMATION: Xaa3 is Asp or Glu
<220> FEATURE:
<221> NAME/KEY: MOD_RES
<222> LOCATION: (5)..(5)
<223> OTHER INFORMATION: Xaa5 is P-Ser, P-Thr, P-homo-Ser,
      4-hydroxyvaline phosphate, P-homo-Thr, P-Cys or P-Tyr
<220> FEATURE:
<221> NAME/KEY: VARIANT
<222> LOCATION: (6)..(6)
<223> OTHER INFORMATION: Xaa6 is any amino acid or Leu
<220> FEATURE:
<221> NAME/KEY: VARIANT
<222> LOCATION: (7)..(7)
<223> OTHER INFORMATION: Xaa7 is Cys
<220> FEATURE:
<221> NAME/KEY: VARIANT
<222> LOCATION: (8)..(8)
<223> OTHER INFORMATION: Xaa8 is any amino acid or Val
<220> FEATURE:
<221> NAME/KEY: VARIANT
<222> LOCATION: (9)..(9)
<223> OTHER INFORMATION: Xaa9 is Asn, Gln, Tyr
<220> FEATURE:
<221> NAME/KEY: VARIANT
<222> LOCATION: (10)..(10)
<223> OTHER INFORMATION: Xaa10 is any amino acid or Val
<220> FEATURE:
<221> NAME/KEY: VARIANT
<222> LOCATION: (11)..(11)
<223> OTHER INFORMATION: Xaa11 is any amino acid or Ala
<220> FEATURE:
<221> NAME/KEY: VARIANT
<222> LOCATION: (13)..(13)
<223> OTHER INFORMATION: Xaa13 is any amino acid or Thr
<220> FEATURE:
<221> NAME/KEY: VARIANT
<222> LOCATION: (14)..(14)
<223> OTHER INFORMATION: Xaa14 is any amino acid or Gly
<220> FEATURE:
<221> NAME/KEY: VARIANT
<222> LOCATION: (15)..(15)
<223> OTHER INFORMATION: Xaa15 is Cys
<220> FEATURE:
<221> NAME/KEY: VARIANT
<222> LOCATION: (16)..(16)
<223> OTHER INFORMATION: Xaa16 is any amino acid, Leu or missing

<400> SEQUENCE: 3

Xaa Xaa Xaa Cys Xaa Xaa Xaa Xaa Xaa Xaa Xaa Cys Xaa Xaa Xaa Xaa
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (2)..(2)
<223> OTHER INFORMATION: Xaa2 is Asp or Glu
<220> FEATURE:
<221> NAME/KEY: VARIANT
<222> LOCATION: (3)..(3)
<223> OTHER INFORMATION: Xaa3 is Asp or Glu
<220> FEATURE:
```

```
<221> NAME/KEY: VARIANT
<222> LOCATION: (4)..(4)
<223> OTHER INFORMATION: Xaa4 is cys or Mpt or Pen or Dpr or Asp or Glu
<220> FEATURE:
<221> NAME/KEY: MOD_RES
<222> LOCATION: (5)..(5)
<223> OTHER INFORMATION: Xaa5 is P-Ser, P-Thr, P-homo-Ser,
      4-hydroxyvaline phosphate, P-homo-Thr, P-Cys or P-Tyr
<220> FEATURE:
<221> NAME/KEY: VARIANT
<222> LOCATION: (7)..(7)
<223> OTHER INFORMATION: Xaa7 is Cys or Mpt or Pen or Dpr or Asp or Glu
<220> FEATURE:
<221> NAME/KEY: VARIANT
<222> LOCATION: (10)..(10)
<223> OTHER INFORMATION: Xaa10 is Val or Pro
<220> FEATURE:
<221> NAME/KEY: VARIANT
<222> LOCATION: (11)..(11)
<223> OTHER INFORMATION: Xaa11 is Ala or Aib
<220> FEATURE:
<221> NAME/KEY: VARIANT
<222> LOCATION: (12)..(12)
<223> OTHER INFORMATION: Xaa12 is Cys or Mpt or Pen or Dpr or Asp or Glu
<220> FEATURE:
<221> NAME/KEY: VARIANT
<222> LOCATION: (14)..(14)
<223> OTHER INFORMATION: Xaa14 is Gly or Ala
<220> FEATURE:
<221> NAME/KEY: VARIANT
<222> LOCATION: (15)..(15)
<223> OTHER INFORMATION: Xaa15 is Cys or Mpt or Pen or Dpr or Asp or Glu

<400> SEQUENCE: 4

Asn Xaa Xaa Xaa Xaa Leu Xaa Val Asn Xaa Xaa Xaa Thr Xaa Xaa Leu
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (6)..(6)
<223> OTHER INFORMATION: Xaa6 is P-Ser, P-thr, P-homo-Ser,
      4-hydroxyvaline phosphate, P-homo-Thr, P-Cys or P-Tyr

<400> SEQUENCE: 5

Lys Pro Gly Thr Cys Xaa Ile Cys Ala Tyr Ala Ala Cys Thr Gly Cys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa5 is P-Ser, P-Thr, P-homo-Ser,
      4-hydroxyvaline phosphate, P-homo-Thr, P-Cys or P-Tyr
<220> FEATURE:
<221> NAME/KEY: VARIANT
<222> LOCATION: (9)..(9)

<400> SEQUENCE: 6

Pro Gly Thr Cys Xaa Ile Cys Ala Tyr Ala Ala Cys Thr Gly Cys
1               5                   10                  15

<210> SEQ ID NO 7
```

```
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa is P-Ser, P-Thr, P-homo-Ser,
      4-hydroxyvaline phosphate, P-homo-Thr, P-Cys or P-Tyr

<400> SEQUENCE: 7

Pro Gly Thr Cys Xaa Ile Cys Ala Ser Ala Ala Cys Thr Gly Cys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa is P-Ser, P-Thr, P-homo-Ser,
      4-hydroxyvaline phosphate, P-homo-Thr, P-Cys or P-Tyr

<400> SEQUENCE: 8

Pro Gly Thr Cys Xaa Ile Cys Ala Thr Ala Ala Cys Thr Gly Cys
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa is P-Ser, P-Thr, P-homo-Ser,
      4-hydroxyvaline phosphate, P-homo-Thr, P-Cys or P-Tyr

<400> SEQUENCE: 9

Pro Gly Thr Cys Xaa Ile Cys Ala Asn Ala Ala Cys Thr Gly Cys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa is P-Ser, P-Thr, P-homo-Ser,
      4-hydroxyvaline phosphate, P-homo-Thr, P-Cys or P-Tyr

<400> SEQUENCE: 10

Pro Gly Thr Cys Xaa Ile Cys Ala Gln Ala Ala Cys Thr Gly Cys
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
```

```
<222> LOCATION: (5)..(5)
<223> OTHER INFORMATION: Xaa is P-Ser, P-Thr, P-homo-Ser,
      4-hydroxyvaline phosphate, P-homo-Thr, P-Cys or P-Tyr

<400> SEQUENCE: 11

Pro Gly Thr Cys Xaa Ile Cys Ala Arg Ala Ala Cys Thr Gly Cys
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa is P-Ser, P-Thr, P-homo-Ser,
      4-hydroxyvaline phosphate, P-homo-Thr, P-Cys or P-Tyr

<400> SEQUENCE: 12

Pro Gly Thr Cys Xaa Ile Cys Ala Glu Ala Ala Cys Thr Gly Cys
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa is P-Ser, P-Thr, P-homo-Ser,
      4-hydroxyvaline phosphate, P-homo-Thr, P-Cys or P-Tyr

<400> SEQUENCE: 13

Pro Gly Thr Cys Xaa Ile Cys Ala Asp Ala Ala Cys Thr Gly Cys
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa is P-Ser, P-Thr, P-homo-Ser,
      4-hydroxyvaline phosphate, P-homo-Thr, P-Cys or P-Tyr

<400> SEQUENCE: 14

Pro Gly Thr Cys Xaa Ile Cys Ala Gly Ala Ala Cys Thr Gly Cys
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa is P-Ser, P-Thr, P-homo-Ser,
      4-hydroxyvaline phosphate, P-homo-Thr, P-Cys or P-Tyr

<400> SEQUENCE: 15

Pro Gly Thr Cys Xaa Ile Cys Ala Ala Ala Ala Cys Thr Gly Cys
```

<210> SEQ ID NO 16
<211> LENGTH: 15
<212> TYPE: PRT
<213> ORGANISM: Artificial Sequence
<220> FEATURE:
<223> OTHER INFORMATION: Synthetically generated sequence
<220> FEATURE:
<221> NAME/KEY: MOD_RES
<222> LOCATION: (5)..(5)
<223> OTHER INFORMATION: Xaa is P-Ser, P-Thr, P-homo-Ser,
      4-hydroxyvaline phosphate, P-homo-Thr, P-Cys or P-Tyr

<400> SEQUENCE: 16

Pro Gly Thr Cys Xaa Ile Cys Ala Met Ala Ala Cys Thr Gly Cys
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa is P-Ser, P-Thr, P-homo-Ser,
      4-hydroxyvaline phosphate, P-homo-Thr, P-Cys or P-Tyr

<400> SEQUENCE: 17

Pro Gly Thr Cys Xaa Ile Cys Ala Ile Ala Ala Cys Thr Gly Cys
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa is P-Ser, P-Thr, P-homo-Ser,
      4-hydroxyvaline phosphate, P-homo-Thr, P-Cys or P-Tyr

<400> SEQUENCE: 18

Pro Gly Thr Cys Xaa Ile Cys Ala Leu Ala Ala Cys Thr Gly Cys
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa is P-Ser, P-Thr, P-homo-Ser,
      4-hydroxyvaline phosphate, P-homo-Thr, P-Cys or P-Tyr

<400> SEQUENCE: 19

Pro Gly Thr Cys Xaa Ile Cys Ala Val Ala Ala Cys Thr Gly Cys
1               5                   10                  15

<210> SEQ ID NO 20
<211> LENGTH: 15
<212> TYPE: PRT
<213> ORGANISM: Artificial Sequence

```
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa is P-Ser, P-Thr, P-homo-Ser,
      4-hydroxyvaline phosphate, P-homo-Thr, P-Cys or P-Tyr

<400> SEQUENCE: 20

Pro Gly Thr Cys Xaa Ile Cys Ala His Ala Ala Cys Thr Gly Cys
1               5                   10                  15

<210> SEQ ID NO 21
<211> LENGTH: 12
<212> TYPE: PRT
<213> ORGANISM: Artificial Sequence
<220> FEATURE:
<223> OTHER INFORMATION: Synthetically generated peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: Xaa5 is P-Ser, P-Thr, P-homo-Ser,
      4-hydroxyvaline phosphate, P-homo-Thr, P-Cys or P-Tyr
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 21

Cys Xaa Xaa Cys Xaa Xaa Xaa Xaa Cys Xaa Xaa Cys
1               5                   10

<210> SEQ ID NO 22
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa1 is Gly, Asn, Pro, Gln, Ser, Thr, Ala, Val,
      Leu, Ile, Met, Phe, Trp, Tyr or is absent
<220> FEATURE:
<221> NAME/KEY: VARIANT
<222> LOCATION: (2)..(2)
<223> OTHER INFORMATION: Xaa2 is Asp, Glu, Gly, His, Asn, Ser, Gln, Thr
      or is absent
<220> FEATURE:
<221> NAME/KEY: VARIANT
<222> LOCATION: (3)..(3)
<223> OTHER INFORMATION: Xaa3 is Thr, Glu, Asp, or Ser
<220> FEATURE:
<221> NAME/KEY: MOD_RES
<222> LOCATION: (5)..(5)
<223> OTHER INFORMATION: Xaa5 is P-Ser, p-Thr, p-homo-Ser,
      4-hydroxyvaline phosphate, P-homo-Thr, P-Cys or P-Tyr
<220> FEATURE:
<221> NAME/KEY: VARIANT
<222> LOCATION: (6)..(6)
<223> OTHER INFORMATION: Xaa6 is Ile or Leu
<220> FEATURE:
<221> NAME/KEY: VARIANT
<222> LOCATION: (8)..(8)
<223> OTHER INFORMATION: Xaa8 is Val, Ile, Ala or Leu
<220> FEATURE:
<221> NAME/KEY: VARIANT
```

```
<222> LOCATION: (9)..(9)
<223> OTHER INFORMATION: Xaa9 is Asn, Tyr, Phe or Gln
<220> FEATURE:
<221> NAME/KEY: VARIANT
<222> LOCATION: (10)..(10)
<223> OTHER INFORMATION: Xaa10 is Val, Ile, Ala, Leu or Pro
<220> FEATURE:
<221> NAME/KEY: VARIANT
<222> LOCATION: (13)..(13)
<223> OTHER INFORMATION: Xaa13 is Ala, Ser or Thr
<220> FEATURE:
<221> NAME/KEY: VARIANT
<222> LOCATION: (14)..(14)
<223> OTHER INFORMATION: Xaa14 is Gly or Ala
<220> FEATURE:
<221> NAME/KEY: VARIANT
<222> LOCATION: (16)..(16)
<223> OTHER INFORMATION: Xaa16 is Leu, Ile, Phe, Trp, Tyr, or is absent
<220> FEATURE:
<221> NAME/KEY: VARIANT
<222> LOCATION: (17)..(17)
<223> OTHER INFORMATION: Xaa17 is Arg, Lys, Ala, Leu, Val, Ile, Ser,
     Thr, Met, Phe, Trp, Tyr, Asp, Glu, Gln Asn or is absent
<220> FEATURE:
<221> NAME/KEY: VARIANT
<222> LOCATION: (18)..(18)
<223> OTHER INFORMATION: Xaa18 is Arg, Lys, Ala, Leu, Val, Ile, Ser,
     Thr, Met, Phe, Trp, Tyr, Asp, Glu, Gln, Asn or is absent

<400> SEQUENCE: 22

Xaa Xaa Xaa Cys Xaa Xaa Cys Xaa Xaa Xaa Ala Cys Xaa Xaa Cys Xaa
1               5                   10                  15

Xaa Xaa

<210> SEQ ID NO 23
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa1 is Gly, Asn, Gln, Thr, or is absent
<220> FEATURE:
<221> NAME/KEY: VARIANT
<222> LOCATION: (2)..(2)
<223> OTHER INFORMATION: Xaa2 is Asp, Glu, or is absent
<220> FEATURE:
<221> NAME/KEY: VARIANT
<222> LOCATION: (3)..(3)
<223> OTHER INFORMATION: Xaa3 is Glu or Asp
<220> FEATURE:
<221> NAME/KEY: MOD_RES
<222> LOCATION: (5)..(5)
<223> OTHER INFORMATION: Xaa10 is p-Ser, p-Thr, p-homo-Ser,
     4-hydroxyvaline phosphate, p-homo-Thr, p-Cys or p-Tyr
<220> FEATURE:
<221> NAME/KEY: VARIANT
<222> LOCATION: (8)..(8)
<223> OTHER INFORMATION: Xaa8 is Val or Ile
<220> FEATURE:
<221> NAME/KEY: VARIANT
<222> LOCATION: (10)..(10)
<223> OTHER INFORMATION: Xaa10 is Val or Ile
<220> FEATURE:
<221> NAME/KEY: VARIANT
<222> LOCATION: (16)..(16)
<223> OTHER INFORMATION: Xaa16 is Leu, Phe, Tyr, or is absent
<220> FEATURE:
<221> NAME/KEY: VARIANT
<222> LOCATION: (17)..(17)
<223> OTHER INFORMATION: Xaa17 is Arg, Lys, Ala, Leu, Val, Ile, Ser,
     Thr, Met, Phe, Trp, Tyr, Asp, Glu, Gln, Asn or is absent
<220> FEATURE:
<221> NAME/KEY: VARIANT
```

```
<222> LOCATION: (18)..(18)
<223> OTHER INFORMATION: Xaa18 is Arg, Lys, Ala, Leu, Val, Ile, Ser,
      Thr, Met, phe, Trp, Tyr, Asp, Glu, Gln, Asn or is absent

<400> SEQUENCE: 23

Xaa Xaa Xaa Cys Xaa Leu Cys Xaa Asn Xaa Ala Cys Thr Gly Cys Xaa
1               5                   10                  15

Xaa Xaa

<210> SEQ ID NO 24
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa1 is Pro, Ser, or is absent
<220> FEATURE:
<221> NAME/KEY: VARIANT
<222> LOCATION: (2)..(2)
<223> OTHER INFORMATION: Xaa2 is Gly, His, Asn, Ser, or is absent
<220> FEATURE:
<221> NAME/KEY: MOD_RES
<222> LOCATION: (5)..(5)
<223> OTHER INFORMATION: Xaa5 is p-Ser, p-Thr, p-homo-Ser,
      4-hydroxyvaline phosphate, p-homo-Thr, p-Cys or p-Tyr
<220> FEATURE:
<221> NAME/KEY: VARIANT
<222> LOCATION: (9)..(9)
<223> OTHER INFORMATION: Xaa9 is Tyr or Phe
<220> FEATURE:
<221> NAME/KEY: VARIANT
<222> LOCATION: (13)..(13)
<223> OTHER INFORMATION: Xaa13 is Ala or Thr
<220> FEATURE:
<221> NAME/KEY: VARIANT
<222> LOCATION: (16)..(16)
<223> OTHER INFORMATION: Xaa16 is Leu, Phe, Tyr, or is absent
<220> FEATURE:
<221> NAME/KEY: VARIANT
<222> LOCATION: (17)..(17)
<223> OTHER INFORMATION: Xaa17 is Arg, Lys, Ala, Leu, Val, Ile, Ser,
      Thr, Met, Phe, Trp, Tyr, Asp, Glu, Gln, Asn or is absent
<220> FEATURE:
<221> NAME/KEY: VARIANT
<222> LOCATION: (18)..(18)
<223> OTHER INFORMATION: Xaa18 is Arg, Lys, Ala, Leu, Val, Ile, Ser,
      Thr, Met, Phe, Trp, Tyr, Asp, Glu, Gln, Asn or is absent

<400> SEQUENCE: 24

Xaa Xaa Thr Cys Xaa Ile Cys Ala Xaa Ala Ala Cys Xaa Gly Cys Xaa
1               5                   10                  15

Xaa Xaa

<210> SEQ ID NO 25
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa1 is Gly, Asn, Pro, Gln, Ser, Thr, Ala,
      Val, Leu, Ile, Met, Phe, Trp, Tyr or is absent
<220> FEATURE:
<221> NAME/KEY: VARIANT
<222> LOCATION: (2)..(2)
<223> OTHER INFORMATION: Xaa2 is Asp, Glu, Gly, His, Asn, Ser, Gln,
      Thr or is absent
<220> FEATURE:
```

```
<221> NAME/KEY: VARIANT
<222> LOCATION: (3)..(3)
<223> OTHER INFORMATION: Xaa3 is Thr, Glu, Asp, or Ser
<220> FEATURE:
<221> NAME/KEY: VARIANT
<222> LOCATION: (6)..(6)
<223> OTHER INFORMATION: Xaa6 is Ile or Leu
<220> FEATURE:
<221> NAME/KEY: VARIANT
<222> LOCATION: (8)..(8)
<223> OTHER INFORMATION: Xaa8 is Val, Ile, Ala, or Leu
<220> FEATURE:
<221> NAME/KEY: VARIANT
<222> LOCATION: (9)..(9)
<223> OTHER INFORMATION: Xaa9 is Asn, Tyr, Phe, or Gln
<220> FEATURE:
<221> NAME/KEY: VARIANT
<222> LOCATION: (10)..(10)
<223> OTHER INFORMATION: Xaa10 is Val, Ile, Ala, Leu or Pro
<220> FEATURE:
<221> NAME/KEY: VARIANT
<222> LOCATION: (13)..(13)
<223> OTHER INFORMATION: Xaa13 is Ala, Ser or Thr
<220> FEATURE:
<221> NAME/KEY: VARIANT
<222> LOCATION: (14)..(14)
<223> OTHER INFORMATION: Xaa14 is Gly or Ala
<220> FEATURE:
<221> NAME/KEY: VARIANT
<222> LOCATION: (16)..(16)
<223> OTHER INFORMATION: Xaa16 is Leu, Ile, Phe, Trp, Tyr, or is absent
<220> FEATURE:
<221> NAME/KEY: VARIANT
<222> LOCATION: (17)..(17)
<223> OTHER INFORMATION: Xaa17 is Arg, Lys, Ala, Leu, Val, Ile, Ser,
      Thr, Met, Phe, Trp, Tyr, Asp, Glu, Gln, Asn or is absent
<220> FEATURE:
<221> NAME/KEY: VARIANT
<222> LOCATION: (18)..(18)
<223> OTHER INFORMATION: Xaa18 is Arg, Lys, Ala, Leu, Val, Ile, Ser,
      Thr, Met, Phe, Trp, Tyr, Asp, Glu, Gln, Asn or is absent

<400> SEQUENCE: 25

Xaa Xaa Xaa Cys Glu Xaa Cys Xaa Xaa Xaa Ala Cys Xaa Xaa Cys Xaa
1               5                   10                  15

Xaa Xaa

<210> SEQ ID NO 26
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa1 is Gly, Asn, Gln, Thr, or is absent
<220> FEATURE:
<221> NAME/KEY: VARIANT
<222> LOCATION: (2)..(2)
<223> OTHER INFORMATION: Xaa2 is Asp, Glu, or is absent
<220> FEATURE:
<221> NAME/KEY: VARIANT
<222> LOCATION: (3)..(3)
<223> OTHER INFORMATION: Xaa3 is Glu or Asp
<220> FEATURE:
<221> NAME/KEY: VARIANT
<222> LOCATION: (8)..(8)
<223> OTHER INFORMATION: Xaa8 is Val or Ile
<220> FEATURE:
<221> NAME/KEY: VARIANT
<222> LOCATION: (10)..(10)
<223> OTHER INFORMATION: Xaa10 is Val or Ile
<220> FEATURE:
<221> NAME/KEY: VARIANT
<222> LOCATION: (16)..(16)
```

```
<223> OTHER INFORMATION: Xaa16 is Leu, Phe, Tyr, or is absent
<220> FEATURE:
<221> NAME/KEY: VARIANT
<222> LOCATION: (17)..(17)
<223> OTHER INFORMATION: Xaa17 is Arg, Lys, Ala, Leu, Val, Ile, Ser,
      Thr, Met, Phe, Trp, Tyr, Asp, Glu, Gln, Asn or is absent
<220> FEATURE:
<221> NAME/KEY: VARIANT
<222> LOCATION: (18)..(18)
<223> OTHER INFORMATION: Xaa9 is Arg, Lys, Ala, Leu, Val, Ile, Ser, Thr,
      Met, Phe, Trp, Tyr, Asp, Glu, Gln, Asn or is absent

<400> SEQUENCE: 26

Xaa Xaa Xaa Cys Glu Leu Cys Xaa Asn Xaa Ala Cys Thr Gly Cys Xaa
1               5                   10                  15

Xaa Xaa

<210> SEQ ID NO 27
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa1 is Pro, Ser, or is absent
<220> FEATURE:
<221> NAME/KEY: VARIANT
<222> LOCATION: (2)..(2)
<223> OTHER INFORMATION: Xaa2 is Gly, His, Asn, Ser, or is absent
<220> FEATURE:
<221> NAME/KEY: VARIANT
<222> LOCATION: (9)..(9)
<223> OTHER INFORMATION: Xaa9 is Tyr or Phe
<220> FEATURE:
<221> NAME/KEY: VARIANT
<222> LOCATION: (13)..(13)
<223> OTHER INFORMATION: Xaa13 is Ala or Thr
<220> FEATURE:
<221> NAME/KEY: VARIANT
<222> LOCATION: (16)..(16)
<223> OTHER INFORMATION: Xaa16 is Leu, Phe, Tyr, or is absent
<220> FEATURE:
<221> NAME/KEY: VARIANT
<222> LOCATION: (17)..(17)
<223> OTHER INFORMATION: Xaa17 is Arg, Lys, Ala, Leu, Val, Ile, Ser,
      Thr, Met, Phe, Trp, Tyr, Asp, Glu, Gln, Asn or is absent
<220> FEATURE:
<221> NAME/KEY: VARIANT
<222> LOCATION: (18)..(18)
<223> OTHER INFORMATION: Xaa18 is Arg, Lys, Ala, Leu, Val, Ile, Ser,
      Thr, Met, Phe, Trp, Tyr, Asp, Glu, Gln, Asn or is absent

<400> SEQUENCE: 27

Xaa Xaa Thr Cys Glu Ile Cys Ala Xaa Ala Ala Cys Xaa Gly Cys Xaa
1               5                   10                  15

Xaa Xaa

<210> SEQ ID NO 28
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa5 is p-Ser
```

```
<400> SEQUENCE: 28

Pro Gly Thr Cys Xaa Ile Cys Ala Tyr Ala Ala Cys Thr Gly Cys
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa5 is p-Ser

<400> SEQUENCE: 29

Asn Asp Asp Cys Xaa Leu Cys Val Asn Val Ala Cys Thr Gly Cys Leu
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: Xaa5 is p-Ser

<400> SEQUENCE: 30

Asn Asp Glu Cys Xaa Leu Cys Val Asn Val Ala Cys Thr Gly Cys Leu
1               5                   10                  15

<210> SEQ ID NO 31
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 31

Asn Thr Phe Tyr Cys Cys Glu Leu Cys Cys Asn Pro Ala Cys Ala Gly
1               5                   10                  15

Cys Tyr

<210> SEQ ID NO 32
<211> LENGTH: 16
<212> TYPE: PRT
<213> ORGANISM: Homo sapiens

<400> SEQUENCE: 32

Asn Asp Asp Cys Glu Leu Cys Val Asn Val Ala Cys Thr Gly Cys Leu
1               5                   10                  15

<210> SEQ ID NO 33
<211> LENGTH: 15
<212> TYPE: PRT
<213> ORGANISM: Homo sapiens

<400> SEQUENCE: 33

Pro Gly Thr Cys Glu Ile Cys Ala Tyr Ala Ala Cys Thr Gly Cys
1               5                   10                  15
```

TREATMENTS FOR GASTROINTESTINAL DISORDERS

PRIORITY CLAIM

This application is a national phase application of PCT/US2012/037663, filed May 11, 2012, which claims priority to U.S. Provisional Patent Application Ser. No. 61/485,060 filed May 11, 2011. The entire contents of the aforementioned applications are incorporated herein by reference.

FIELD OF THE INVENTION

This invention relates to peptides, compositions and methods for treating gastrointestinal disorders.

SEQUENCE LISTING

This application incorporates by reference in its entirety the Sequence Listing entitled "IW109PCT1a_sequence_ST25.txt" (22.3 kilobytes), which was last modified on Jul. 11, 2014 and filed electronically herewith.

BACKGROUND

Functional dyspepsia (FD) and gastroparesis (GP) are upper gastrointestinal (GI) disorders that are collectively characterized by symptoms that include bloating, epigastric (upper abdominal) pain and/or burning, nausea, vomiting and early satiation. Therapeutic options for FD and GP patients are extremely limited, due to both lack of efficacy and poor safety profiles for existing therapies. Dyspepsia is defined as the presence of one or more dyspepsia symptoms (epigastric pain, burning, bothersome postprandial fullness, and early satiation) that are considered to originate from the gastroduodenal region, in the absence of any organic, systemic, or metabolic disease that is likely to explain the symptoms (see Drossman, D. A., ed., Rome III: The Functional Gastrointestinal Disorders, 3rd Ed., McLean, Va.: Degnon Associates, Inc., 2006). FD refers to dyspepsia that has no structural explanation after standard medical investigations, including upper endoscopy. Pathophysiological mechanisms that may be involved in FD include, among others, delayed gastric emptying, impaired gastric accommodation, hypersensitivity to gastric distention, altered duodenal sensitivity to lipids or acid, and abnormal duodenojejunal motility. Prolonged duodenal acid exposure is also seen in some FD and GP patients, and this exposure may slow gastric emptying and cause FD or GP-like symptoms. Dyspepsia is a common syndrome that accounts for about 30% of cases seen by gastroenterologists, with FD representing about 60% of all such dyspepsia cases.

GP refers to abnormal gastric motility characterized by delayed gastric emptying in the absence of mechanical obstruction. GP may be idiopathic or may be caused by various conditions, including Type I or Type II diabetes mellitus, viral infection, scleroderma, nervous system disorders such as Parkinson's disease, metabolic disorders such as hypothyroidism, post-operative ileus, and certain medications, including narcotic pain medications, tricyclic antidepressants and calcium channel blockers. Treatment for cancer, including chemotherapeutic drugs and radiation to the chest and abdomen can also cause gastroparesis, either temporarily or permanently. The most common symptoms are nausea, vomiting, bloating, epigastric pain, weight loss and early satiation. Gastroparesis is a chronic condition that can lead to frequent hospitalization, decreased quality of life, and increased disability and, in severe cases, increased mortality. Severe, symptomatic GP is common in individuals suffering from diabetes, affecting from 5-10% of diabetics for a total patient population of 1 million in the U.S. alone.

Constipation-predominant irritable bowel syndrome (IBS-C) and chronic constipation (CC) are common lower gastrointestinal (GI) disorders. IBS-C is characterized by symptoms that include recurrent abdominal pain or discomfort, fewer than three bowel movements per week, lumpy or hard stools, defecation straining, a feeling of incomplete bowel movement, passing mucus and/or bloating (Drossman et al., Rome III: The Functional Gastrointestinal Disorders, 3rd Ed., McLean, Va.: Degnon Assoc., Inc., 2006). Chronic constipation (also called functional constipation) is characterized by defecation straining, lumpy or hard stools, sensation of incomplete evacuation, sensation of anorectal obstruction/blockage, and/or fewer than three bowel movements per week (Drossman 2006).

Inflammatory bowel disease (IBD) refers to a group of gastrointestinal (GI) disorders characterized by active inflammation of the colon and/or small intestine. The main forms of IBD are ulcerative colitis (UC) and Crohn's disease but also include collagenous colitis, lymphocytic colitis, ischemic colitis, diversion colitis, Behçet's syndrome and infective colitis. UC is restricted to the colon and the rectum while Crohn's disease can affect the entire GI tract, although most cases affect the lower part of the GI tract, starting in the terminal ileum and affecting the lower small intestine, colon and rectum. In addition, UC is restricted to the epithelial lining of the gut, while Crohn's disease can affect the whole bowel wall. Both UC and Crohn's disease can cause abdominal pain and diarrhea and may increase the risk of colorectal cancer. It is estimated that up to one million people in the US are affected by IBD, with male and female patients appearing to be equally affected.

About 10% of Americans older than 40 and about half of all people older than 60 have diverticulosis, which is a condition in which small pouches in the lining of the colon bulge outward through weak spots. These pouches, called diverticula, are most common in the lower portion of the colon. About 10 to 25% of people with diverticulosis develop diverticulitis, which is an inflammation or infection of the diverticula. Symptoms of diverticulitis include abdominal pain, fever, nausea and a change in bowel habits, and complications include bleeding, bowel perforations and blockages in the colon.

Colorectal cancer, also called colon cancer or large bowel cancer, refers to cancerous growths in the colon and rectum. Colorectal cancer is the fourth most common form of cancer in the US and is responsible for 655,000 deaths worldwide per year. Although colorectal cancer may be cured if found before it has metastasized, it often is not diagnosed until there has been significant metastasis, because it may cause no symptoms. Uroguanylin and guanylin levels, which are the natural ligands of GC-C, are decreased or lost in colorectal cancer and activation of GC-C reverse the tumorigenic phenotype of colorectal cancer cells. Thus, it has been suggested that colon cancer may be treated or prevented with oral supplementation with GC-C agonists (Li et al., Curr. Mol. Pharmacol. 2:285-92, 2009). Conventional treatment options for FD and GP, IBS-C, CC, IBD, diverticulitis, colorectal cancer as well as other disorder have been of limited efficacy for many patients. Thus, there remains a need for new compounds and methods for treating these disorders.

SUMMARY

The present invention features peptides, compositions, and related methods for treating upper gastrointestinal disorders and conditions (e.g., FD, GP, post-operative gastric ileus, a functional esophageal disorder, a functional gastroduodenal disorder, gastroesophageal reflux disease (GERD), or a duodenal or stomach ulcer) as well as other conditions and disorders such as IBS-C, CC, IBD, diverticulitis, colorectal cancer that are described herein.

The compositions of the instant invention feature peptides that comprise phosphoamino acid substitutions at a certain position of the amino acid sequence. In a certain embodiment the phosphoamino acid is at the 5 position of the Uroguanylin (Ugn) peptide sequence, including P-Ser, P-Thr, P-homo-Ser, 4-hydroxyvaline phosphate, P-homo-Thr, P-Cys or P-Tyr. In another embodiment the phosphoamino acid is at the 5 position of the Guanylin peptide sequence, including P-Ser, P-Thr, P-homo-Ser, 4-hydroxyvaline phosphate, P-homo-Thr, P-Cys or P-Tyr. In one embodiment the phosphoamino acid is at the 5 position of the Guanilib (Plecanatide) peptide sequence, including P-Ser, P-Thr, P-homo-Ser, 4-hydroxyvaline phosphate, P-homo-Thr, P-Cys or P-Tyr.

The compositions of the instant invention feature phosphorylated peptides that activate guanylate cyclase C (GC-C) in the upper GI but activate GC-C in the lower GI much more weakly or not at all. Without being bound by any particular theory, the peptides of the invention are useful because they may alleviate symptoms of upper GI disorders (in whole or in part by increasing upper GI motility and/or reducing epigastric pain/discomfort and bloating) without causing pronounced effects in the lower GI tract (e.g., dose-limiting alterations in bowel habits, including diarrhea) at dose levels and dosing frequency sufficient to reduce upper GI symptoms. The peptides of the invention are also useful for ameliorating gastrointestinal pain and discomfort.

In one aspect, the invention features a polypeptide comprising, consisting of, or consisting essentially of the amino acid sequence: $Xaa_1$ $Xaa_2$ $Xaa_3$ $Cys_4$ $Xaa_5$ $Xaa_6$ $Xaa_7$ $Xaa_8$ $Xaa_9$ $Xaa_{10}$ $Xaa_{11}$ $Cys_{12}$ $Xaa_{13}$ $Xaa_{14}$ $Xaa_{15}$ $Xaa_{16}$ [SEQ ID NO: 1] wherein:
  $Xaa_1$ is Ser, Asn, Tyr, Ala, Gln, Pro, Lys, Gly, or Thr, or is missing;
  $Xaa_2$ is His, Asp, Glu, Ala, Ser, Asn, Gly, or is missing;
  $Xaa_3$ is Thr, Asp, Ser, Glu, Pro, Val or Leu;
  $Xaa_5$ is P-Ser, P-Thr, P-homo-Ser, 4-hydroxyvaline phosphate, P-homo-Thr, P-Cys or P-Tyr;
  $Xaa_6$ is Ile, Trp or Leu;
  $Xaa_7$ is Cys, Ser, or Tyr;
  $Xaa_8$ is Ala, Val, Thr, Ile, Met or is missing;
  $Xaa_9$ is a) any amino acid, b) Phe, Tyr, Asn, Trp, c) an amino acid other than Phe, Trp, or Tyr, d) non-aromatic amino acid or e) is missing;
  $Xaa_{10}$ is Ala, Val, Met, Thr or Ile;
  $Xaa_{11}$ is Ala or Val;
  $Xaa_{13}$ is Ala or Thr;
  $Xaa_{14}$ is Gly, Ala or Ser;
  $Xaa_{15}$ is Cys, Tyr or is missing; and
  $Xaa_{16}$ is: a) Trp, Tyr or Phe to create a chymotrypsin cleavage site; b) Lys or Arg to create a trypsin cleavage site; c) is missing or d) His or Leu or Ser.

In certain embodiments, $Xaa_1$ is preceded by Lys or Tyr. In certain embodiments, a Cys is replaces by any amino acid other than Cys. Certain such polypeptides will have fewer disulfide bonds.

In a related aspect the invention features a composition comprising a polypeptide comprising, consisting of, or consisting essentially of the amino acid sequence: $Xaa_1$ $Xaa_2$ $Xaa_3$ $Cys_4$ $Xaa_5$ $Xaa_6$ $Xaa_7$ $Xaa_8$ $Xaa_9$ $Xaa_{10}$ $Xaa_{11}$ $Cys_{12}$ $Xaa_{13}$ $Xaa_{14}$ $Xaa_{15}$ $Xaa_{16}$ [SEQ ID NO: 2] wherein:
  $Xaa_1$ is Ser, Asn, Tyr, Ala, Gln, Pro, Lys, Gly, or Thr, or is missing;
  $Xaa_2$ is His, Asp, Glu, Ala, Ser, Asn, Gly, Pro or is missing;
  $Xaa_3$ is Thr, Asp, Ser, Glu, Pro, Val or Leu;
  $Xaa_5$ is P-Ser, P-Thr, P-homo-Ser, 4-hydroxyvaline phosphate, P-homo-Thr, P-Cys or P-Tyr;
  $Xaa_6$ is Ile, Trp or Leu; $Xaa_7$ is Cys, Ser, or Tyr;
  $Xaa_8$ is Ala, Val, Thr, Ile, Met or is missing; $Xaa_9$ is Phe, Tyr, Asn, Trp, an amino acid other than Phe, Trp, or Tyr, is a non-aromatic amino acid or is missing;
  $Xaa_{10}$ is Ala, Val, Met, Thr or Ile;
  $Xaa_{11}$ is Ala or Val;
  $Xaa_{13}$ is Ala or Thr;
  $Xaa_{14}$ is Gly, Ala or Ser;
  $Xaa_{15}$ is Cys, Tyr or is missing; and
  $Xaa_{16}$ is: a) Trp, Tyr or Phe to create a chymotrypsin cleavage site; b) Lys or Arg to create a trypsin cleavage site; c) is missing or d) His or Leu or Ser and a pharmaceutically acceptable carrier. In related aspects, the invention features a pharmaceutically acceptable tablet, pill, capsule comprising the peptide.

In a related aspect, the invention features a polypeptide comprising, consisting of, or consisting essentially of the amino acid sequence: $Xaa_1$ $Xaa_2$ $Xaa_3$ $Cys_4$ $Xaa_5$ $Xaa_6$ $Xaa_7$ $Xaa_8$ $Xaa_9$ $Xaa_{10}$ $Xaa_{11}$ $Cys_{12}$ $Xaa_{13}$ $Xaa_{14}$ $Xaa_{15}$ $Xaa_{16}$ [SEQ ID NO: 3] wherein:
  $Xaa_1$ is Asn, any amino acid or is missing;
  $Xaa_2$ is Asp, Glu, any amino acid or is missing;
  $Xaa_3$ is Asp or Glu;
  $Xaa_5$ is P-Ser, P-Thr, P-homo-Ser, 4-hydroxyvaline phosphate, P-homo-Thr, P-Cys or P-Tyr;
  $Xaa_6$ is any amino acid or Leu;
  $Xaa_7$ is Cys;
  $Xaa_8$ is any amino acid or Val;
  $Xaa_9$ is Asn, Gln, Tyr;
  $Xaa_{10}$ is any amino acid or Val;
  $Xaa_{11}$ is any amino acid or Ala;
  $Xaa_{13}$ is any amino acid or Thr;
  $Xaa_{14}$ is any amino acid or Gly;
  $Xaa_{15}$ is Cys;
  $Xaa_{16}$ is any amino acid, Leu or missing.

In a related aspect, the invention features a polypeptide comprising, consisting of, or consisting essentially of the amino acid sequence $Asn_1$ $Xaa_2$ $Xaa_3$ $Xaa_4$ $Xaa_5$ $Leu_6$ $Xaa_7$ $Val_8$ $Asn_9$ $Xaa_{10}$ $Xaa_{11}$ $Xaa_{12}$ $Thr_{13}$ $Xaa_{14}$ $Xaa_{15}$ $Leu_{16}$ [SEQ ID NO: 4] wherein:
  $Xaa_2$ is Asp or Glu;
  $Xaa_3$ is Asp or Glu;
  $Xaa_4$ is Cys or Mpt (mercaptoproline) or Pen (penicillamine) or Dpr (diaminopropionic acid) or Asp or Glu;
  $Xaa_5$ is P-Ser, P-Thr, P-homo-Ser, 4-hydroxyvaline phosphate, P-homo-Thr, P-Cys or P-Tyr;
  $Xaa_7$ is Cys or Mpt (mercaptoproline) or Pen (penicillamine) or Dpr (diaminopropionic acid) or Asp or Glu;
  $Xaa_{10}$ is Val or Pro;
  $Xaa_{11}$ is Ala or Aib (alpha-aminoisobutyric acid);
  $Xaa_{12}$ is Cys or Mpt (mercaptoproline) or Pen (penicillamine) or Dpr (diaminopropionic acid) or Asp or Glu;
  $Xaa_{14}$ is Gly or Ala;
  $Xaa_{15}$ is Cys or Mpt (mercaptoproline) or Pen (penicillamine) or Dpr (diaminopropionic acid) or Asp or Glu.

In certain embodiments, where $Xaa_{15}$ is other than Cys or is missing, $Xaa_7$ is Ser or an amino acid other than Cys and $Xaa_5$ is P-Ser, P-Thr, P-homo-Ser, 4-hydroxyvaline phosphate, P-homo-Thr, P-Cys or P-Tyr.

In certain embodiments 1, 2, 3, 4, 5, 6, 7, 8, 9, 10, 11 or 12 of $Xaa_1$, $Xaa_2$, $Xaa_3$, $Xaa_5$, $Xaa_6$, $Xaa_7$, $Xaa_8$, $Xaa_9$, $Xaa_{10}$, $Xaa_{11}$, $Xaa_{13}$, $Xaa_{14}$, and $Xaa_{16}$ are any amino acid other than Cys, and $Xaa_5$ is P-Ser, P-Thr, P-homo-Ser, 4-hydroxyvaline phosphate, P-homo-Thr, P-Cys or P-Tyr.

In certain embodiments, $Xaa_9$ is any amino acid other than Gln and $Xaa_5$ is P-Ser, P-Thr, P-homo-Ser, 4-hydroxyvaline phosphate, P-homo-Thr, P-Cys or P-Tyr. In other embodiments where $Xaa_2$ and $Xaa_3$ are Glu, $Xaa_9$ is any amino acid other than Gln and $Xaa_5$ is P-Ser, P-Thr, P-homo-Ser, 4-hydroxyvaline phosphate, P-homo-Thr, P-Cys or P-Tyr.

In certain embodiments $Xaa_1$ and $Xaa_2$ are missing; $Xaa_3$ is Thr; $Xaa_5$ is P-Ser, P-Thr, P-homo-Ser, 4-hydroxyvaline phosphate, P-homo-Thr, P-Cys or P-Tyr; $Xaa_6$ is Ile or Leu; $Xaa_8$ is Ala, Val, or Ile; $Xaa_9$ is Phe or Tyr; $Xaa_{10}$ is Ala or Val; $Xaa_{11}$ is Ala; $Xaa_{13}$ is Ala or Thr; $Xaa_{14}$ is Gly; and $Xaa_{16}$ is Trp, Tyr, Phe, Lys, Arg or is missing.

In certain embodiments the polypeptide comprising, consisting of, or consisting essentially of the amino acid sequence: $Xaa_1$ $Xaa_2$ $Xaa_3$ $Cys_4$ $Xaa_5$ $Xaa_6$ $Xaa_7$ $Xaa_8$ $Xaa_9$ $Xaa_{10}$ $Xaa_{11}$ $Cys_{12}$ $Xaa_{13}$ $Xaa_{14}$ $Xaa_{15}$ $Xaa_{16}$ [SEQ ID NO:1] is not cleaved after $Xaa_9$ by chymotrypsin. In these embodiments wherein:

$Xaa_1$ is Ser, Asn, Tyr, Ala, Gln, Pro, Lys, Gly, or Thr, or is missing;
$Xaa_2$ is His, Asp, Glu, Ala, Ser, Asn, or Gly, or is missing;
$Xaa_3$ is Thr, Asp, Ser, Glu, Pro, Val or Leu or is missing;
$Xaa_5$ is P-Ser, P-Thr, P-homo-Ser, 4-hydroxyvaline phosphate, P-homo-Thr, P-Cys or P-Tyr;
$Xaa_6$ is Ile, Trp or Leu;
$Xaa_7$ is Cys, Ser, or Tyr;
$Xaa_8$ is Ala, Val, Thr, Ile, Met or is missing;
$Xaa_9$ is either: a) any amino acid other than Phe and Tyr, b) any amino acid other than Phe, Tyr, and Trp, c) any amino acid other than Phe, Tyr, Trp, Ile, Leu and Val; d) any amino acid other than Phe, Tyr, Trp, Ile, Leu, Val, and His; d) any non-aromatic amino acid or e) is missing;
$Xaa_{10}$ is Ala, Val, Met, Thr or Ile;
$Xaa_{11}$ is Ala or Val;
$Xaa_{13}$ is Ala or Thr;
$Xaa_{14}$ is Gly, Ala or Ser;
$Xaa_{15}$ is Cys, Tyr or is missing; and
$Xaa_{16}$ is: a) Trp, Tyr or Phe to create a chymotrypsin cleavage site; b) Lys or Mg to create a trypsin cleavage site; c) is missing or d) His or Leu or Ser.

In addition, the invention features variants of $Xaa_1$ $Xaa_2$ $Xaa_3$ $Cys_4$ $Xaa_5$ $Xaa_6$ $Xaa_7$ $Xaa_8$ $Xaa_9$ $Xaa_{10}$ $Xaa_{11}$ $Cys_{12}$ $Xaa_{13}$ $Xaa_{14}$ $Xaa_{15}$ $Xaa_{16}$ [SEQ ID NO:1] that is not cleaved after $Xaa_9$ by chymotrypsin due to the addition of an amino terminal lysine and $Xaa_5$ is P-Ser, P-Thr, P-homo-Ser, 4-hydroxyvaline phosphate, P-homo-Thr, P-Cys or P-Tyr. An example of such a molecule is a human guanylin variant having an amino terminal lysine: KPGTCXaaICAYAACTGC [SEQ ID NO: 5] and wherein Xaa is P-Ser, P-Thr, P-homo-Ser, 4-hydroxyvaline phosphate, P-homo-Thr, P-Cys or P-Tyr.

In certain embodiments of the peptide comprising, consisting of, or consisting essentially of the amino acid sequence: $Xaa_1$ $Xaa_2$ $Xaa_3$ $Cys_4$ $Xaa_5$ $Xaa_6$ $Xaa_7$ $Xaa_8$ $Xaa_9$ $Xaa_{10}$ $Xaa_{11}$ $Cys_{12}$ $Xaa_{13}$ $Xaa_{14}$ $Xaa_{15}$ $Xaa_{16}$ [SEQ ID NO:1] that is not cleaved after $Xaa_9$ by chymotrypsin, $Xaa_7$ and $Xaa_{15}$ are both Cys and $Xaa_5$ is P-Ser, P-Thr, P-homo-Ser, 4-hydroxyvaline phosphate, P-homo-Thr, P-Cys or P-Tyr.

Also within the invention are variants of PGTCXaa-ICAYAACTGC [SEQ ID NO: 6] (human guanylin) wherein Y is substituted by any amino acid other than a) Phe; b) any amino acid other than Phe and Trp; c) any amino acid other than Phe, Trp, Ile, Leu and Val; d) any amino acid other than Phe, Trp, Ile, Leu, Val and His; e) any non-aromatic amino acid, f) is missing or and Xaa is P-Ser, P-Thr, P-homo-Ser, 4-hydroxyvaline phosphate, P-homo-Thr, P-Cys or P-Tyr.

In certain embodiments the polypeptide comprising, consisting of, or consisting essentially of the amino acid sequence: $Xaa_1$ $Xaa_2$ $Xaa_3$ $Cys_4$ $Xaa_5$ $Xaa_6$ $Xaa_7$ $Xaa_8$ $Xaa_9$ $Xaa_{10}$ $Xaa_{11}$ $Cys_{12}$ $Xaa_{13}$ $Xaa_{14}$ $Xaa_{15}$ $Xaa_{16}$ [SEQ ID NO:1] is not cleaved after $Xaa_9$ by either chymotrypsin or trypsin. In these embodiments wherein:

$Xaa_1$ is Ser, Asn, Tyr, Ala, Gln, Pro, Lys, Gly, or Thr, or is missing;
$Xaa_2$ is His, Asp, Glu, Ala, Ser, Asn, or Gly, or is missing;
$Xaa_3$ is Thr, Asp, Ser, Glu, Pro, Val or Leu or is missing;
$Xaa_5$ is P-Ser, P-Thr, P-homo-Ser, 4-hydroxyvaline phosphate, P-homo-Thr, P-Cys or P-Tyr;
$Xaa_6$ is Ile, Trp or Leu;
$Xaa_7$ is Cys, Ser, or Tyr;
$Xaa_8$ is Ala, Val, Thr, Ile, Met or is missing;
$Xaa_9$ is either: a) any amino acid other than Lys, Arg, Phe and Tyr, b) any amino acid other than Lys, Arg, Phe, Tyr, and Trp, c) any amino acid other than Lys, Arg, Phe, Tyr, Trp, Ile, Leu and Val; d) any amino acid other than Lys, Arg, Phe, Tyr, Trp, He, Leu, Val, and His; or e) is missing;
$Xaa_{10}$ is Ala, Val, Met, Thr or Ile;
$Xaa_{11}$ is Ala or Val;
$Xaa_{13}$ is Ala or Thr;
$Xaa_{14}$ is Gly, Ala or Ser;
$Xaa_{15}$ is Cys, Tyr or is missing; and
$Xaa_{16}$ is: a) Trp, Tyr or Phe to create a chymotrypsin cleavage site; b) Lys or Arg to create a trypsin cleavage site; c) is missing or d) His or Leu or Ser.

In certain embodiments of the peptide comprising, consisting of, or consisting essentially of the amino acid sequence: $Xaa_1$ $Xaa_2$ $Xaa_3$ $Cys_4$ $Xaa_5$ $Xaa_6$ $Xaa_7$ $Xaa_8$ $Xaa_9$ $Xaa_{10}$ $Xaa_{11}$ $Cys_{12}$ $Xaa_{13}$ $Xaa_{14}$ $Xaa_{15}$ $Xaa_{16}$ [SEQ ID NO:1] that is not cleaved after $Xaa_9$ by chymotrypsin or trypsin, $Xaa_7$ and $Xaa_{15}$ are both Cys and $Xaa_5$ is P-Ser, P-Thr, P-homo-Ser, 4-hydroxyvaline phosphate, P-homo-Thr, P-Cys or P-Tyr.

Useful variants of PGTCXaaICAYAACTGC [SEQ ID NO: 6] (human guanylin) that should not be cleaved by chymotrypsin include:

PGTCXaaICASAACTGC [SEQ ID NO: 7]

PGTCXaaICATAACTGC [SEQ ID NO: 8]

PGTCXaaICANAACTGC [SEQ ID NO: 9]

PGTCXaaICAQAACTGC [SEQ ID NO: 10]

PGTCXaaICARAACTGC [SEQ ID NO: 11]

PGTCXaaICAEAACTGC [SEQ ID NO: 12]

PGTCXaaICADAACTGC [SEQ ID NO: 13]

PGTCXaaICAGAACTGC [SEQ ID NO: 14]

```
                                    [SEQ ID NO: 15]
            PGTCXaaICAAAACTGC

[SEQ ID NO: 16]
            PGTCXaaICAMAACTGC
``` and wherein Xaa is P-Ser, P-Thr, P-homo-Ser, 4-hydroxyvaline phosphate, P-homo-Thr, P-Cys or P-Tyr.

Additional variants which are not likely to be cleaved by chymotrypsin under certain conditions include:

```
                                    [SEQ ID NO: 17]
            PGTCXaaICAIAACTGC

[SEQ ID NO: 18]
            PGTCXaaICALAACTGC

[SEQ ID NO: 19]
            PGTCXaaICAVAACTGC

[SEQ ID NO: 20]
            PGTCXaaICAHAACTGC
``` and wherein Xaa is P-Ser, P-Thr, P-homo-Ser, 4-hydroxyvaline phosphate, P-homo-Thr, P-Cys or P-Tyr.

In one aspect, the invention features a pharmaceutical composition comprising the B isomer of a guanylin family peptide that comprises phosphoamino acid substitutions. In one embodiment, the guanylin family peptide is the B isomer of an uroguanylin (Ugn) peptide or a guanylin (Gn) peptide that comprises phosphoamino acid substitutions. In another embodiment, the guanylin family peptide that comprises phosphoamino acid substitutions is UgnB or GnB. In another embodiment, the guanylin family peptide that comprises phosphoamino acid substitutions is UgnB (e.g., huUgnB) at a ratio of UgnB:UgnA of between 55:45 and 100:0 (e.g., a ratio of UgnB:UgnA of 55:45, 60:40, 65:35, 70:30, 75:25, 80:20, 85:15, 90:10, 95:5, 99:1, or greater). In another embodiment, the guanylin family peptide that comprises phosphoamino acid substitutions is GnB (e.g., huGnB) at a ratio of GnB:GnA of between 55:45 and 100:0 (e.g., a ratio of GnB:GnA of 55:45, 60:40, 65:35, 70:30, 75:25, 80:20, 85:15, 90:10, 95:5, 99:1, or greater). In one embodiment, the pharmaceutical composition is lyophilized. In certain embodiments the phosphoamino acid substitution is at the 5 position of the amino acid sequence. In certain embodiments the phosphoamino acid is P-Ser, P-Thr, P-homo-Ser, 4-hydroxyvaline phosphate, P-homo-Thr, P-Cys or P-Tyr.

The invention also features a pharmaceutical composition comprising UgnB (e.g., huUgnB) modified to decrease the rate of conversion of UgnB to UgnA and modified to comprise phosphoamino acid substitutions. The invention also features a pharmaceutical composition comprising a GnB (e.g., huGnB) modified to decrease the rate of conversion of GnB to GnA and modified to comprise phosphoamino acid substitutions.

The invention features a method for treating a disorder characterized by fluid retention in a subject, by administering an effective amount of composition comprising the peptides of the invention that are modified to comprise phosphoamino acid substitutions, such as modified UgnB (e.g., huUgnB) alone, or present at a non-naturally occurring ratio with optionally modified UgnA (e.g., a ratio of UgnB:UgnA of 55:45, 60:40, 65:35, 70:30, 75:25, 80:20, 85:15, 90:10, 95:5, 99:1, or greater). The invention features a method for treating a disorder characterized by fluid retention in a subject by administering an effective amount of composition comprising GnB (e.g., huGnB) modified to comprise phosphoamino acid substitutions in the absence of GbA, or present at a non-naturally occurring ratio with optionally modified GnA (e.g., a ratio of GnB:GnA of 55:45, 60:40, 65:35, 70:30, 75:25, 80:20, 85:15, 90:10, 95:5, 99:1, or greater).

If desired, in addition to the phosphoamino acid modification UgnB can be modified to decrease the rate of conversion to UgnA. Also, if present in the composition, in addition to the phosphoamino acid modification UgnA can be modified to prevent conversion to UgnB. UgnB can contain amino acid substitutions, including conserved or non-naturally occurring amino-acids. The peptide can have, for example, the following sequence: Asn Asp Glu Cys Xaa Leu Cys Val Asn Val Ala Cys Thr Gly Cys Leu wherein Xaa is P-Ser, P-Thr, P-homo-Ser, 4-hydroxyvaline phosphate, P-homo-Thr, P-Cys or P-Tyr.

Similarly, if desired, in addition to the phosphoamino acid modification GnB can be modified to decrease the rate of conversion to GnA. Also, if present in the composition, in addition to the phosphoamino acid modification GnA can be modified to prevent conversion to GnB. The GnB sequence can contain further amino acid substitutions, including conserved or non-naturally occurring amino-acids.

As used herein, a guanylin family peptide is a peptide having a naturally occurring or non-naturally occurring amino acid sequence with four cysteines arranged in a characteristic pattern (Cys-Xaa-Xaa-Cys-Xaa$_5$-Xaa-Xaa-Xaa-Cys-Xaa-Xaa-Cys [SEQ ID NO: 21]) wherein Xaa$_5$ a phosphorylated amino acid such as P-Ser, P-Thr, P-homo-Ser, 4-hydroxyvaline phosphate, P-homo-Thr, P-Cys or P-Tyr [SEQ ID NO: 21].

In one embodiment, a guanylin family peptide contains two disulfide bonds, one between the first Cys and the third Cys and one between the second Cys and the fourth Cys.

In one embodiment, the A form of guanylin family peptides bind to and activate guanylate cyclase-C receptor. Guanylin family peptides include, inter alia, guanylin, uroguanylin, lymphoguanylin, and renoguanylin peptides.

In one embodiment, guanylin family peptides include guanylin and uroguanylin peptides.

In a further embodiment, guanylin family peptides include mammalian guanylin and uroguanylin peptides.

In another embodiment, guanylin family peptides comprise the sequence Xaa$_1$-Xaa$_2$-Xaa$_3$-Cys$_4$-Xaa$_5$-Xaa$_6$-Cys$_7$-Xaa$_8$-Xaa$_9$-Xaa$_{10}$-Ala$_{11}$-Cys$_{12}$-Xaa$_{13}$-Xaa$_{14}$-Cys$_{15}$-Xaa$_{16}$-Xaa$_{17}$-Xaa$_{18}$ [SEQ ID NO: 22]; wherein Xaa$_1$ is Gly, Asn, Pro, Gln, Ser, Thr, Ala, Val, Leu, Ile, Met, Phe, Trp, Tyr or is absent;

Xaa$_2$ is Asp, Glu, Gly, His, Asn, Ser, Gln, Thr or is absent;

Xaa$_3$ is Thr, Glu, Asp, or Ser;

Xaa$_5$ is P-Ser, P-Thr, P-homo-Ser, 4-hydroxyvaline phosphate, P-homo-Thr, P-Cys or P-Tyr;

Xaa$_6$ is Ile or Leu;

Xaa$_8$ is Val, Ile, Ala, or Leu;

Xaa$_9$ is Asn, Tyr, Phe, or Gln;

Xaa$_{10}$ is Val, Ile, Ala, Leu or Pro;

Xaa$_{13}$ is Ala, Ser or Thr;

Xaa$_{14}$ is Gly or Ala;

Xaa$_{16}$ is Leu, Ile, Phe, Trp, Tyr, or is absent;

Xaa$_{17}$ is Arg, Lys, Ala, Leu, Val, Ile, Ser, Thr, Met, Phe, Trp, Tyr, Asp, Glu, Gln, Asn or is absent; and Xaa$_{18}$ is Arg, Lys, Ala, Leu, Val, Ile, Ser, Thr, Met, Phe, Trp, Tyr, Asp, Glu, Gln, Asn or is absent.

"Uroguanylin B" or "UgnB" means a polypeptide having the following sequence: Xaa$_1$-Xaa$_2$-Xaa$_3$-Cys$_4$-Xaa$_5$-Leu$_6$-Cys$_7$-Xaa$_8$-Asn$_9$-Xaa$_{10}$-Ala$_{11}$-Cys$_{12}$-Thr$_{13}$-Gly$_{14}$-Cys$_{15}$-Xaa$_{16}$-Xaa$_{17}$-Xaa$_{18}$ [SEQ ID NO: 23]; where Xaa$_1$ is Gly, Asn, Gln, Thr, or is absent;
Xaa$_2$ is Asp, Glu, or is absent;
Xaa$_3$ is Glu or Asp;
Xaa$_5$ is P-Ser, P-Thr, P-homo-Ser, 4-hydroxyvaline phosphate, P-homo-Thr, P-Cys or P-Tyr.
Xaa$_8$ is Val or Ile;
Xaa$_{10}$ is Val or Ile;
Xaa$_{16}$ is Leu, Phe, Tyr, or is absent;
Xaa$_{17}$ is Arg, Lys, Ala, Leu, Val, Ile, Ser, Thr, Met, Phe, Trp, Tyr, Asp, Glu, Gln, Asn or is absent; and
Xaa$_{18}$ is Arg, Lys, Ala, Leu, Val, Ile, Ser, Thr, Met, Phe, Trp, Tyr, Asp, Glu, Gln, Asn or is absent.

The carboxy-terminal amino acid, whether it be Xaa$_{16}$, Xaa$_{17}$, or Xaa$_{18}$ can be either a D-amino acid or an L-amino acid, and is optionally amidated.

"Guanylin B" or "GnB" means a polypeptide having the following sequence: Xaa$_1$-Xaa$_2$-Thr$_3$-Cys$_4$-Xaa$_5$-Ile$_6$-Cys$_7$-Ala$_8$-Xaa$_9$-Ala$_{10}$-Ala$_{11}$-Cys$_{12}$-Xaa$_{13}$-Gly$_{14}$-Cys$_{15}$-Xaa$_{16}$-Xaa$_{17}$-Xaa$_{18}$ [SEQ ID NO: 24]; where
Xaa$_1$ is Pro, Ser, or is absent;
Xaa$_2$ is Gly, His, Asn, Ser, or is absent;
Xaa$_5$ is P-Ser, P-Thr, P-homo-Ser, 4-hydroxyvaline phosphate, P-homo-Thr, P-Cys or P-Tyr
Xaa$_9$ is Tyr or Phe;
Xaa$_{13}$ is Ala or Thr;
Xaa$_{16}$ is Leu, Phe, Tyr, or is absent;
Xaa$_{17}$ is Arg, Lys, Ala, Leu, Val, Ile, Ser, Thr, Met, Phe, Trp, Tyr, Asp, Glu, Gln, Asn or is absent; and
Xaa$_{18}$ is Arg, Lys, Ala, Leu, Val, Ile, Ser, Thr, Met, Phe, Trp, Tyr, Asp, Glu, Gln, Asn or is absent.

The carboxy-terminal amino acid, whether it be Xaa$_{17}$ or Xaa$_{18}$, can be either a D amino acid or an L-amino acid, and is optionally amidated.

A second aspect of the present invention provides pharmaceutical compositions comprising a peptide of the present invention.

A third aspect of the present invention provides methods for treating a gastrointestinal disorder, which include administering a pharmaceutical composition according to the present invention.

The details of one or more embodiments of the invention are set forth in the accompanying description.

DETAILED DESCRIPTION

Guanylate cyclase C (GC-C) is a transmembrane receptor that is located on the apical surface of epithelial cells in the stomach and intestine. The receptor has an extracellular ligand-binding domain, a single transmembrane region and a C-terminal guanylyl cyclase domain. When a ligand binds to the extracellular domain of GC-C, the intracellular catalytic domain catalyzes the production of cGMP from GTP. In vivo, this increase in intracellular cGMP initiates a cascade of events that leads to increased secretion of chloride and bicarbonate into the intestinal lumen, increased luminal pH, decreased luminal sodium absorption, increased fluid secretion, and acceleration of intestinal transit. cGMP, which is secreted bidirectionally from the epithelium into the mucosa and lumen, has also been shown to dampen afferent C fiber firing, suggesting a potential mechanism for the observed analgesic effects of GC-C agonists on visceral pain.

Linaclotide, a peptide GC-C agonist that is orally administered and currently in clinical trials for treatment of irritable bowel syndrome with constipation (IBS-c) and chronic constipation (CC), has numerous effects on lower GI physiology including: (1) reduced visceral pain, (2) reduced bloating, and (3) increased GI transit, which can lead to increased stool frequency and improved stool consistency. Orally administered linaclotide acts locally by activating GC-C at the luminal surface; there are no detectable levels of linaclotide seen systemically after oral administration at therapeutic dose levels. Thus, the results from clinical trials of linaclotide, as well as preclinical studies that have been done with linaclotide and related peptides, suggest that GC-C peptide agonists may be used therapeutically.

Ugn and Guanylin (Gn) are 13-16 amino acid peptides that share a distinctive ring structure produced by two disulfide bonds: one disulfide bond between the first and the third cysteines of the core guanylin family peptide motif and a second disulfide bond between the second and the fourth cysteines of the core guanylin family peptide motif. For example, in huUgn the ring structure is formed by disulfide bonds between the cysteines at positions 4 and 12 and positions 7 and 15. A flexible peptide backbone allows the carboxy terminus to be positioned either above or below the plane of this ring, leading to the existence of two conformationally distinct stereoisomers, termed UgnA and UgnB.

This type of isomerism is unique among mammalian peptides and in the rat, mouse, and opossum interconversions between the two conformations of Gn and Ugn occur at a rate of 1-2 cycles per sec at 37° C. and neutral pH. While the structure and interconversion rate of human Gn is similar to its rat counterpart, human Ugn has an additional leucine residue that extends the C terminus and sterically hinders the transition between the A and B conformations, increasing the half-life of each form to about 2 days at 37° C. Because of this relative stability, human UgnA and UgnB can be separated by HPLC and tested independently for activity. In such studies, UgnA elicits robust responses when applied to cultured GC-C-expressing cells, with an $E_{C50}$ on the order of $1^{0-7}$ M, while UgnB is more than 100-fold less potent.

The invention comprises administration of the B isomer of guanylin family peptides. This guanylin family peptide can be purified human Uroguanylin B (huUgnB) or it can be huUgnB or another guanylin family peptide modified to stabilize the B-isoform.

A guanylin family peptide is a peptide having a naturally occurring or non-naturally occurring amino acid sequence with four cysteines arranged in a characteristic pattern (Cys-Xaa-Xaa-Cys-Xaa-Xaa-Xaa-Xaa-Cys-Xaa-Xaa-Cys [SEQ ID NO: 21]), for example, the guanylin family peptide can contain the following sequence:
Xaa$_1$-Xaa$_2$-Xaa$_3$-Cys$_4$-Glu$_5$-Xaa$_6$-Cys$_7$-Xaa$_8$-Xaa$_9$-Xaa$_{10}$-Ala$_{11}$-Cys$_{12}$-Xaa$_{13}$-Xaa$_{14}$-Cys$_{15}$-Xaa$_{16}$-Xaa$_{17}$-Xaa$_{18}$ [SEQ ID NO: 25]; wherein
Xaa$_1$ is Gly, Asn, Pro, Gln, Ser, Thr, Ala, Val, Leu, Ile, Met, Phe, Trp, Tyr or is absent;
Xaa$_2$ is Asp, Glu, Gly, His, Asn, Ser, Gln, Thr or is absent;
Xaa$_3$ is Thr, Glu, Asp, or Ser;
Xaa$_6$ is Ile or Leu;
Xaa$_8$ is Val, Ile, Ala, or Leu;
Xaa$_9$ is Asn, Tyr, Phe, or Gln;
Xaa$_{10}$ is Val, Ile, Ala, Leu or Pro;
Xaa$_{13}$ is Ala, Ser or Thr;
Xaa$_{14}$ is Gly or Ala;
Xaa$_{16}$ is Leu, Ile, Phe, Trp, Tyr, or is absent;
Xaa$_{17}$ is Arg, Lys, Ala, Leu, Val, Ile, Ser, Thr, Met, Phe, Trp, Tyr, Asp, Glu, Gln, Asn or is absent;
and Xaa$_{18}$ is Arg, Lys, Ala, Leu, Val, Ile, Ser, Thr, Met, Phe, Trp, Tyr, Asp, Glu, Gln, Asn or is absent.

The A form of guanylin family peptides can bind to and activate guanylate cyclase-C receptor (GC-C receptor). Guanylin family peptides include, guanylin (Gn), uroguanylin (Ugn), lymphoguanylin, and renoguanylin peptides.

Ugn can have the sequence:

Xaa$_1$-Xaa$_2$-Xaa$_3$-Cys$_4$-Glu$_5$-Leu$_6$-Cys$_7$-Xaa$_8$-Asn$_9$-Xaa$_{10}$-Ala$_{11}$-Cys$_{12}$-Thr$_{13}$-Gly$_{14}$-Cys$_{18}$-Xaa$_{16}$-Xaa$_{17}$-Xaa$_{18}$ [SEQ ID NO: 26]; where Xaa$_1$ is Gly, Asn, Gln, Thr, or is absent;
Xaa$_2$ is Asp, Glu, or is absent;
Xaa$_3$ is Glu or Asp;
Xaa$_8$ is Val or Ile;
Xaa$_{10}$ is Val or Ile;
Xaa$_{16}$ is Leu, Phe, Tyr, or is absent;
Xaa$_{17}$ is Arg, Lys, Ala, Leu, Val, Ile, Ser, Thr, Met, Phe, Trp, Tyr, Asp, Glu, Gln, Asn or is absent; and
Xaa$_{18}$ is Arg, Lys, Ala, Leu, Val, Ile, Ser, Thr, Met, Phe, Trp, Tyr, Asp, Glu, Gln, Asn or is absent.

The carboxy-terminal amino acid, whether it be Xaa$_7$, Xaa$_8$, or Xaa$_9$ can be either a D-amino acid or an L-amino acid, and is optionally amidated.

huUgn has the sequence: Asn Asp Asp Cys Glu Leu Cys Val Asn Val Ala Cys Thr Gly Cys Leu [SEQ ID NO: 32]

Guanylin can have the sequence:

Xaa$_1$-Xaa$_2$-Thr$_3$-Cys$_4$-Glu$_5$-Ile$_6$-Cys$_7$-Ala$_8$-Xaa$_9$-Ala$_{10}$-Ala$_{11}$-Cys$_{12}$-Xaa$_{13}$-Gly$_{14}$-Cys$_{15}$-Xaa$_{16}$-Xaa$_{17}$-Xaa$_{18}$ [SEQ ID NO: 27]; where Xaa$_1$ is Pro, Ser, or is absent;
Xaa$_2$ is Gly, His, Asn, Ser, or is absent;
Xaa$_9$ is Tyr or Phe;
Xaa$_{13}$ is Ala or Thr;
Xaa$_{16}$ is Leu, Phe, Tyr, or is absent;
Xaa$_{17}$ is Arg, Lys, Ala, Leu, Val, Ile, Ser, Thr, Met, Phe, Trp, Tyr, Asp, Glu, Gln, Asn or is absent; and
Xaa$_{18}$ is Arg, Lys, Ala, Leu, Val, Ile, Ser, Thr, Met, Phe, Trp, Tyr, Asp, Glu, Gln, Asn or is absent.

The carboxy-terminal amino acid, whether it be Xaa$_{17}$ or Xaa$_{18}$, can be either a D-amino acid or an L-amino acid, and is optionally amidated.

huGn has the sequence: Pro Gly Thr Cys Glu Ile Cys Ala Tyr Ala Ala Cys Thr Gly Cys [SEQ ID NO: 33].

Further sequences of Ugn and Gn are set forth in PCT Application Publication No. WO2007/101158, which is hereby incorporated by reference in its entirety.

It would be useful to have a GC-C agonist that could be used to alleviate upper GI disorders and symptoms (e.g., functional dyspepsia (FD) and gastroparesis (GP)) without promoting pronounced effects on bowel habits that could result from stimulation of GC-C in lower parts of the GI tract. Such a GC-C agonist would decrease the potential for lower GI adverse events, including altered bowel habits and diarrhea. The GC-C peptide agonists described herein are more active in the upper GI tract (e.g., the stomach and duodenum), and less active in the lower GI tract. Such agonists would have benefits in patients who suffer from upper GI disorders (e.g., FD and GP) by (1) reducing visceral pain through cGMP production and or/other mechanisms, (2) decreasing bloating, (3) increasing gastric emptying and/or upper small intestine transit (e.g., duodenal transit), and (4) neutralizing acid in the duodenum by promoting bicarbonate secretion. Importantly, these agonists, by virtue of their targeted activity to the upper GI, would be able to alleviate the symptoms of FD and GP without causing pronounced effects on bowel habits (e.g., that can result from stimulation of GC-C in lower parts of the GI tract).

In one aspect, the invention provides a novel GC-C peptide agonist useful for the treatment of gastrointestinal disorders, particularly upper GI disorders such as FD and GP. The GC-C peptide agonist is designed to be active in the upper GI, including the esophagus, stomach and upper small intestine (duodenum) but to be less active as it traverses the rest of the small intestine and large intestine. The peptides of the invention are also useful for ameliorating gastrointestinal pain and discomfort. The GC-C agonist peptide contains a phosphoamino acid, e.g., a phosphoserine, to replace a conserved glutamate or aspartate found in other GC-C agonist peptides. The phosphate of a phosphoamino acid —OPO$_3^{2-}$, such as phosphoserine, is able to act as a biomimetic for the COO" of glutamate or aspartate such that the phosphoamino acid-containing peptide is able to bind to and activate GC-C. The phosphoamino acid-containing peptide can be dephosphorylated by intestinal alkaline phosphatases, which greatly decreases the GC-C binding and agonist activity of the peptide. Intestinal alkaline phosphatases are found throughout the GI tract, and are most active in an alkaline luminal environment, including the small intestine. The phosphoamino acid-containing peptide is able to activate GC-C in the upper GI tract, including the acidic stomach environment and upper GI tract, to promote fluid and bicarbonate secretion. As the peptide promotes increased fluid and bicarbonate secretion in the upper GI, the intestinal lumen becomes more alkaline, thus activating the alkaline phosphatase activity. Thus, through the action of the peptide on GC-C as well as the movement of the peptide through the intestine, the peptide's phosphoamino acid is converted to the dephosphorylated amino acid, thereby decreasing its activity as a GC-C agonist as it transits from the upper to lower GI.

As used herein, the term "P-" preceding an amino acid or the three letter abbreviation thereof, refers to a phosphoamino acid. For example, the terms "P-Ser", "P-Thr", "P-Tyr", "P-Cys", "P-homo-Cys", "P-homo-Ser" and "P-homo-Thr" refer to phosphoserine, phosphothreonine, phosphotyrosine, phosphocysteine, phosphohomocysteine, phosphohomoserine, and phosphohomothreonine, respectively. As used herein, a phosphoamino acid refers to an ester or thioester of an amino acid and phosphoric acid; e.g., the hydrogen on the alcohol or thiol functional group is replaced by —P(O)(OH)$_2$. For example, P-Ser has the structure

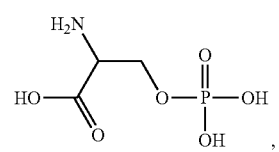 [SMILES: NC(COP(=O)(O)O)C(=O)O]

P-Thr has the structure

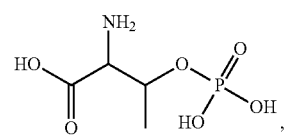

P-Tyr has the structure

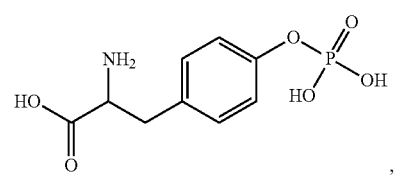 [SMILES: NC(Cc1ccc(OP(=O)(O)O)cc1)C(=O)O]

and P-Cys has the structure

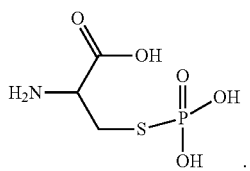

In one aspect, the present invention provides a peptide or a pharmaceutically acceptable salt thereof, wherein the peptide comprises, consists of or consists essentially of the amino acid sequence:
$Xaa_1$-$Xaa_2$-$Xaa_3$-$Cys_4$-$Xaa_5$-$Xaa_6$-$Cys_7$-$Xaa_8$-$Xaa_9$-$Xaa_{10}$-$Ala_{11}$-$Cys_{12}$-$Xaa_{13}$-$Xaa_{14}$-$Cys_{15}$-$Xaa_{16}$-$Xaa_{17}$-$Xaa_{18}$ [SEQ ID NO: 22]; wherein $Xaa_1$ is Gly, Asn, Pro, Gln, Ser, Thr, Ala, Val, Leu, Ile, Met, Phe, Trp, Tyr or is absent;
$Xaa_2$ is Asp, Glu, Gly, His, Asn, Ser, Gln, Thr or is absent;
$Xaa_3$ is Thr, Glu, Asp, or Ser;
$Xaa_5$ is P-Ser, P-Thr, P-homo-Ser, 4-hydroxyvaline phosphate, P-homo-Thr, P-Cys or P-Tyr
$Xaa_6$ is Ile or Leu;
$Xaa_8$ is Val, Ile, Ala, or Leu;
$Xaa_9$ is Asn, Tyr, Phe, or Gln;
$Xaa_{10}$ is Val, Ile, Ala, Leu or Pro;
$Xaa_{13}$ is Ala, Ser or Thr;
$Xaa_{14}$ is Gly or Ala;
$Xaa_{16}$ is Leu, Ile, Phe, Trp, Tyr, or is absent;
$Xaa_{17}$ is Arg, Lys, Ala, Leu, Val, Ile, Ser, Thr, Met, Phe, Trp, Tyr, Asp, Glu, Gln, Asn or is absent; and
$Xaa_{18}$ is Arg, Lys, Ala, Leu, Val, Ile, Ser, Thr, Met, Phe, Trp, Tyr, Asp, Glu, Gln, Asn or is absent.

In one aspect, the present invention provides a peptide or a pharmaceutically acceptable salt thereof, wherein the peptide comprises, consists of or consists essentially of the amino acid sequence:
$Xaa_1$-$Xaa_2$-$Xaa_3$-$Cys_4$-$Xaa_5$-$Xaa_6$-$Cys_7$-$Xaa_8$-$Xaa_9$-$Xaa_{10}$-$Ala_{11}$-$Cys_{12}$-$Xaa_{13}$-$Xaa_{14}$-$Cys_{15}$-$Xaa_{16}$-$Xaa_{17}$-$Xaa_{18}$ [SEQ ID NO: 22]; wherein $Xaa_1$ is Gly, Asn, Pro, Gln, Ser, Thr, or is absent;
$Xaa_2$ is Asp, Glu, Gly, His, Asn, Ser, or is absent;
$Xaa_3$ is Thr, Glu, or Asp;
$Xaa_5$ is P-Ser, P-Thr, P-homo-Ser, 4-hydroxyvaline phosphate, P-homo-Thr, P-Cys or P-Tyr
$Xaa_6$ is Ile or Leu;
$Xaa_8$ is Val, Ile, or Ala;
$Xaa_9$ is Asn, Tyr, or Phe;
$Xaa_{10}$ is Val, Ile, or Ala;
$Xaa_{13}$ is Ala or Thr;
$Xaa_{14}$ is Gly;
$Xaa_{16}$ is Leu, Phe, Tyr, or is absent;
$Xaa_{17}$ is Arg, Lys, Ala, Leu, Val, Ile, Ser, Thr, Met, Phe, Trp, Tyr, Asp, Glu, Gln, Asn or is absent; and
$Xaa_{18}$ is Arg, Lys, Ala, Leu, Val, Ile, Ser, Thr, Met, Phe, Trp, Tyr, Asp, Glu, Gln, Asn or is absent.

In one aspect, the present invention provides a peptide or a pharmaceutically acceptable salt thereof, wherein the peptide comprises, consists of or consists essentially of the amino acid sequence:
$Xaa_1$-$Xaa_2$-$Xaa_3$-$Cys_4$-$Xaa_5$-$Xaa_6$-$Cys_7$-$Xaa_8$-$Xaa_9$-$Xaa_{10}$-$Ala_{11}$-$Cys_{12}$-$Xaa_{13}$-$Xaa_{14}$-$Cys_{15}$-$Xaa_{16}$-$Xaa_{17}$-$Xaa_{18}$ [SEQ ID NO: 22]; wherein $Xaa_1$ is Pro, Ser, or is absent;
$Xaa_2$ is Gly, His, Asn, Ser, or is absent;

$Xaa_3$ is Thr;
$Xaa_5$ is P-Ser, P-Thr, P-homo-Ser, 4-hydroxyvaline phosphate, P-homo-Thr, P-Cys or P-Tyr
$Xaa_6$ is Ile;
$Xaa_8$ is Ala;
$Xaa_9$ is Tyr or Phe;
$Xaa_{10}$ is Ala;
$Xaa_{13}$ is Ala or Thr;
$Xaa_{14}$ is Gly;
$Xaa_{16}$ is Leu, Phe, Tyr, or is absent;
$Xaa_{17}$ is Arg, Lys, Ala, Leu, Val, Ile, Ser, Thr, Met, Phe, Trp, Tyr, Asp, Glu, Gln, Asn or is absent; and
$Xaa_{18}$ is Arg, Lys, Ala, Leu, Val, Ile, Ser, Thr, Met, Phe, Trp, Tyr, Asp, Glu, Gln, Asn or is absent.

In one aspect, the present invention provides a peptide or a pharmaceutically acceptable salt thereof, wherein the peptide comprises, consists of or consists essentially of the amino acid sequence:
$Xaa_1$-$Xaa_2$-$Xaa_3$-$Cys_4$-$Xaa_5$-$Xaa_6$-$Cys_7$-$Xaa_8$-$Xaa_9$-$Xaa_{10}$-$Ala_{11}$-$Cys_{12}$-$Xaa_{13}$-$Xaa_{14}$-$Cys_{15}$-$Xaa_{16}$-$Xaa_{17}$-$Xaa_{18}$ [SEQ ID NO: 22] wherein $Xaa_1$ is Pro, Ser, or is absent;
$Xaa_2$ is Gly, His, Asn, Ser, or is absent;
$Xaa_3$ is Thr;
$Xaa_5$ is P-Ser, P-Thr, P-homo-Ser, 4-hydroxyvaline phosphate, P-homo-Thr, P-Cys or P-Tyr;
$Xaa_6$ is Ile;
$Xaa_8$ is Ala;
$Xaa_9$ is Tyr or Phe;
$Xaa_{10}$ is Ala;
$Xaa_{33}$ is Ala or Thr;
$Xaa_{14}$ is Gly;
$Xaa_{16}$ is Leu, Phe, Tyr, or is absent;
$Xaa_{17}$ is Arg, Lys, Ala, Val, Leu, Ile or is absent; and
$Xaa_{18}$ is Arg, Lys, Ala, Val, Leu, Ile or is absent.

In one aspect, the present invention provides a peptide or a pharmaceutically acceptable salt thereof, wherein the peptide comprises, consists of or consists essentially of the amino acid sequence:
$Xaa_1$-$Xaa_2$-$Xaa_3$-$Cys_4$-$Xaa_5$-$Xaa_6$-$Cys_7$-$Xaa_8$-$Xaa_9$-$Xaa_{10}$-$Ala_{11}$-$Cys_{12}$-$Xaa_{13}$-$Xaa_{14}$-$Cys_{15}$-$Xaa_{16}$-$Xaa_{17}$-$Xaa_{18}$ [SEQ ID NO: 22]; wherein $Xaa_1$ is Gly, Asn, Gln, Thr, or is absent;
$Xaa_2$ is Asp, Glu, or is absent;
$Xaa_3$ is Glu or Asp;
$Xaa_5$ is P-Ser, P-Thr, P-homo-Ser, 4-hydroxyvaline phosphate, P-homo-Thr, P-Cys or P-Tyr;
$Xaa_6$ is Leu;
$Xaa_8$ is Val or Ile;
$Xaa_9$ is Asn;
$Xaa_{10}$ is Val or Ile;
$Xaa_{13}$ is Thr;
$Xaa_{14}$ is Gly;
$Xaa_{16}$ is Leu, Phe, Tyr or is absent;
$Xaa_{17}$ is Arg, Lys, Ala, Leu, Val, Ile, Ser, Thr, Met, Phe, Trp, Tyr, Asp, Glu, Gln, Asn or is absent; and
$Xaa_{18}$ is Arg, Lys, Ala, Leu, Val, Ile, Ser, Thr, Met, Phe, Trp, Tyr, Asp, Glu, Gln, Asn or is absent.

In one aspect, the present invention provides a peptide or a pharmaceutically acceptable salt thereof, wherein the peptide comprises, consists of or consists essentially of the amino acid sequence:
$Xaa_1$-$Xaa_2$-$Xaa_3$-$Cys_4$-$Xaa_5$-$Xaa_6$-$Cys_7$-$Xaa_8$-$Xaa_9$-$Xaa_{10}$-$Ala_{11}$-$Cys_{12}$-$Xaa_{13}$-$Xaa_{14}$-$Cys_{15}$-$Xaa_{16}$-$Xaa_{17}$-$Xaa_{18}$ [SEQ ID NO: 22]; wherein $Xaa_1$ is Gly, Asn, Gln, Thr, or is absent;
$Xaa_2$ is Asp, Glu, or is absent;

Xaa$_3$ is Glu or Asp;
Xaa$_5$ is P-Ser, P-Thr, P-homo-Ser, 4-hydroxyvaline phosphate, P-homo-Thr, P-Cys or P-Tyr;
Xaa$_6$ is Leu;
Xaa$_8$ is Val or Ile;
Xaa$_9$ is Asn;
Xaa$_{10}$ is Val or Ile;
Xaa$_{13}$ is Thr;
Xaa$_{14}$ is Gly;
Xaa$_{16}$ is Leu, Phe, Tyr, or is absent;
Xaa$_{17}$ is Arg, Lys, Ala, Val, Leu, Ile or is absent; and
Xaa$_{18}$ is Arg, Lys, Ala, Val, Leu, Ile or is absent.

In one aspect, the present invention provides a peptide or a pharmaceutically acceptable salt thereof, wherein the peptide comprises, consists of or consists essentially of the amino acid sequence:

```
                                              [SEQ ID NO: 28]
Pro Gly Thr Cys P-Ser Ile Cys Ala Tyr Ala Ala Cys

Thr Gly Cys;
                                              [SEQ ID NO: 29]
Asn Asp Asp Cys P-Ser Leu Cys Val Asn Val Ala Cys

Thr Gly Cys Leu;
or
                                              [SEQ ID NO: 30]
Asn Asp Glu Cys P-Ser Leu Cys Val Asn Val Ala Cys

Thr Gly Cys Leu.
```

In some embodiments, a peptide or pharmaceutically acceptable salt thereof is provided, wherein the peptide comprises peptide comprises no more than 50, 40, 30 or 20 amino acids. In further embodiments, the peptide comprises no more than 19, 18, 17, 16, 15 or 14 amino acids.

Variant Peptides

In some circumstances it can be desirable to treat patients with a variant peptide that binds to and activates intestinal GC-C receptors, but is less active or more active than the non-variant form of the peptide. Reduced activity can arise from reduced affinity for the receptor or a reduced ability to activate the receptor once bound or reduced stability of the peptide. Increased activity can arise from increased affinity for the receptor or an increased ability to activate the receptor once bound or increased stability of the peptide.

In some peptides one or both members of one or both pairs of Cys residues which normally form a disulfide bond can be replaced by homocysteine, penicillamine, 3-mercaptoproline (Kolodziej et al. 1996 *Int J Pept Protein Res* 48:274); β,β-dimethylcysteine (Hunt et al. 1993 *Int J Pept Protein Res* 42:249) or diaminopropionic acid (Smith et al. 1978 *J Med Chem* 21:117) to form alternative internal cross-links at the positions of the normal disulfide bonds.

In other embodiments, the disulfide bonds may be replaced by hydrocarbon crosslinking (Schafmeister et al. 2000 J Am Chem Sac 122:5891, Patgiri et al. 2008 Acc Chem Res 41:1289, Henchey et al. 2008 Curr Opin Chem Biol 12:692).

Production of Peptides

In one embodiment, peptides or precursor peptides of the invention can be produced recombinantly in any known protein expression system, including, without limitation, bacteria (e.g., *E. coli* or *Bacillus subtilis*), insect cell systems (e.g., *Drosophila* Sf9 cell systems), yeast cell systems (e.g., *S. cerevisiae, S. saccharomyces*) or filamentous fungal expression systems, or animal cell expression systems (e.g., mammalian cell expression systems). Peptides or precursor peptides of the invention may also be chemically synthesized.

If the peptide or variant peptide is to be produced recombinantly, e.g., *E. coli*, the nucleic acid molecule encoding the peptide may also encode a leader sequence that permits the secretion of the mature peptide from the cell. Thus, the sequence encoding the peptide can include the pre-sequence and the pro-sequence of, for example, a naturally-occurring bacterial ST peptide. The secreted, mature peptide can be purified from the culture medium.

The sequence encoding a peptide described herein is can be inserted into a vector capable of delivering and maintaining the nucleic acid molecule in a bacterial cell. The DNA molecule may be inserted into an autonomously replicating vector (suitable vectors include, for example, pGEM3Z and pcDNA3, and derivatives thereof). The vector nucleic acid may be a bacterial or bacteriophage DNA such as bacteriophage lambda or Ml 3 and derivatives thereof. Construction of a vector containing a nucleic acid described herein can be followed by transformation of a host cell such as a bacterium. Suitable bacterial hosts include but are not limited to, *E. coli, B. subtilis, Pseudomonas* and *Salmonella*. The genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art. The expression vector can also include a translation regulatory sequence (e.g., an untranslated 5' sequence, an untranslated 3' sequence, or an internal ribosome entry site). The vector can be capable of autonomous replication or it can integrate into host DNA to ensure stability during peptide production.

The protein coding sequence that includes a peptide described herein can also be fused to a nucleic acid encoding a peptide affinity tag, e.g., glutathione S-transferase (GST), maltose E binding protein, protein A, FLAG tag, hexa-histidine, myc tag or the influenza HA tag, in order to facilitate purification. The affinity tag or reporter fusion joins the reading frame of the peptide of interest to the reading frame of the gene encoding the affinity tag such that a translational fusion is generated. Expression of the fusion gene results in translation of a single peptide that includes both the peptide of interest and the affinity tag. In some instances where affinity tags are utilized, DNA sequence encoding a protease recognition site will be fused between the reading frames for the affinity tag and the peptide of interest.

Genetic constructs and methods suitable for production of immature and mature forms of the peptides and variants described herein in protein expression systems other than bacteria, and well known to those skilled in the art, can also be used to produce peptides in a biological system.

Peptides produced recombinantly may be phosphorylated using methods known to those skilled in the art. In some embodiments, a peptide is recombinantly produced, isolated from the cell in which it was expressed, and then phosphorylated using a protein kinase, e.g., a serine/threonine kinase or a tyrosine kinase. A large number of kinases are known in the art and may be used for this purpose. One skilled in the art will recognize that different kinases have differing substrate specificities and will pick a kinase to use based upon the sequence of the peptide. In other embodiments, a peptide is recombinantly produced in a cell that also expresses a serine/threonine kinase or tyrosine kinase that will phosphorylate the peptide. In other embodiments, peptides may be recombinantly produced by incorporating a phosphoamino acid.

Methods for modifying tRNA including, but not limited to, modifying the anti-codon, the amino acid attachment site, and/or the accepter stem to allow incorporation of unnatural and/or arbitrary amino acids are known in the art (Biochem. Biophys. Res. Comm. (2008) 372: 480-485; Chem. Biol. (2009) 16:323-36; Nat. Methods (2007) 4:239-44; Nat. Rev. Mol. Cell Biol. (2006) 7:775-82; Methods (2005) 36:227-238; Methods (2005) 36:270-278; Annu. Rev. Biochem. (2004) 73:147-176; Nuc. Acids Res. (2004) 32:6200-6211; Proc. Natl. Acad. Sci. USA (2003) 100:6353-6357; Royal Soc. Chem. (2004) 33:422-430).

In some embodiments, peptides may be chemically produced. Peptides can be synthesized by a number of different methods including solution and solid phase synthesis using traditional BOC or FMOC protection. For example, the peptide can be synthesized on 2-Chlorotritylchloride or Wang resin using consecutive amino acid couplings. The following protecting groups can be used: Fluorenylmethyloxycarbonyl or tert-butyloxycarbonyl (alpha-amino groups, N-terminus); trityl or tert-butyl (thiol groups of Cy); tert-butyl (γ-carboxyl of glutamic acid and the hydroxyl group of threonine, if present); trityl (β-amid function of the asparagine side chain and the phenolic group of tyrosine, if present); trityl or tert-butyldimethylsilyl (hydroxygroup of serine, if present) and tert-Butyloxycarbonyl (N-terminus prior to subsequent side chain modifications). Coupling can be effected with DIC and HOBt in the presence of a tertiary amine, and the peptide can be deprotected and cleaved from the solid support in using cocktail K (trifluoroacetic acid 81%, phenol 5%, thioanisole 5%, 1,2-ethanedithiol 2.5%, water 3%, dimethylsulphide 2%, ammonium iodide 1.5% w/w). After removal of trifluoroacetic acid and other volatiles the peptide can be precipitated using an organic solvent. Disulfide bonds between Cys residues can be formed using dimethyl sulfoxide (Tam et al. (1991) J. Am. Chem. Soc. 113:6657-62) or using an air oxidation strategy. The resulting peptide can be purified by reverse-phase chromatography and lyophilized.

A phosphoamino acid, e.g., a phosphoserine, may be introduced into a peptide by any method known to one skilled in the art (see, e.g., G. K. Toth et al. (2007), Current Organic Chemistry 11: 409-426). In some embodiments, a protected phosphoamino acid analogue, e.g., a phosphoserine amino acid analogue, can be introduced as part of the peptide assembly on solid phase; e.g. as Fmoc-Ser[PO(OBzl)OH]-OH (T. Wakamiya et al. (1997), Bioorganic and Medicinal Chemistry 5: 135-145, 1997) or as Fmoc-Ser[PO(OAryl/Alkyl)$_2$]-OH (G. K. Toth et al. (2007) Current Organic Chemistry, 11: 409-426). In another embodiment, a protected amino acid analogue, e.g., a protected serine amino acid analogue, can be introduced as part of the peptide assembly on solid phase (e.g. Fmoc-protected serine with a trityl protection for the hydroxyl side chain). After full assembly of the peptide chain Ser[Trt] or Ser[SiMe$_2$tBu] can be selectively deprotected and the phosphate group can be introduced using a phosphoramidite/oxidation strategy (G. Shapiro et al. (1994) Tetrahedron Letters 35: 869-872; P. Hormozdiari et al. (1996) Tetrahedron Letters, 37: 8227-8230).

In other embodiments, a chemically produced peptide may be phosphorylated using a serine/threonine kinase or tyrosine kinase as described above.

Peptides can be made, isolated or used either in form of the free base or as pharmaceutically acceptable salts thereof. Examples of salts include, without limitation, acetate, chloride, sulfate and phosphate salts of the peptide.

Compositions of Peptides and GC-C Receptor Agonists

In another aspect, compositions are provided wherein the peptides, alone or in combination, can be combined with any pharmaceutically acceptable carrier or medium. The peptides can be combined with materials that do not produce an adverse, allergic or otherwise unwanted reaction when administered to a patient. The carriers or mediums used can include solvents, dispersants, coatings, absorption promoting agents, controlled release agents, and one or more inert excipients (which include starches, polyols, granulating agents, microcrystalline cellulose (e.g., celphere, Celphere Beads®), diluents, lubricants, binders, disintegrating agents, and the like), etc. If desired, tablet dosages of the disclosed compositions may be coated by standard aqueous or non-aqueous techniques.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

As used herein, the term "binder" refers to any pharmaceutically acceptable binder that may be used in the practice of the invention. Examples of pharmaceutically acceptable binders include, without limitation, a starch (e.g., corn starch, potato starch and pre-gelatinized starch (e.g., STARCH 1500® and STARCH 1500 LM®, sold by Colorcon, Ltd.) and other starches), maltodextrin, gelatin, natural and synthetic gums such as acacia, powdered tragacanth, guar gum, cellulose and its derivatives (e.g., methylcellulose, hydroxyethyl cellulose, hydroxyethyl methylcellulose, hydroxypropyl cellulose and hydroxypropyl methylcellulose (hypromellose), ethyl cellulose, cellulose acetate, carboxymethyl cellulose calcium, sodium carboxymethyl cellulose, carboxymethylcellulose, powdered cellulose, microfine cellulose, microcrystalline cellulose (e.g. AVICEL™, such as, AVICEL-PH-101™, -103™ and -105™, sold by FMC Corporation, Marcus Hook, Pa., USA)), polyvinyl alcohol, polyvinyl pyrrolidone (e.g., polyvinyl pyrrolidone K30), and mixtures thereof.

Examples of binders that may be particularly used in pharmaceutical compositions include polyvinyl alcohol, polyvinylpyrrolidone (povidone), a starch, maltodextrin or a cellulose ether (such as, for example, methylcellulose, ethylcellulose, carboxymethylcellulose, hydroxyethyl cellulose, hydroxyethyl methylcellulose, hydroxypropyl cellulose and hydroxypropyl methylcellulose).

As used herein, the term "filler" refers to any pharmaceutically acceptable filler that may be used in the practice of the invention. Examples of pharmaceutically acceptable fillers include, without limitation, talc, calcium carbonate (e.g., granules or powder), dibasic calcium phosphate, tribasic calcium phosphate, calcium sulfate (e.g., granules or powder), microcrystalline cellulose (e.g., Avicel PH101 or Celphere CP-305), microfine cellulose, powdered cellulose, dextrates, kaolin, mannitol, silicic acid, sorbitol, starch (e.g., Starch 1500), pre-gelatinized starch, lactose, glucose, fructose, galactose, trehalose, sucrose, maltose, isomalt, raffinose, maltitol, melezitose, stachyose, lactitol, palatinite, xylitol, myoinositol, and mixtures thereof.

Examples of pharmaceutically acceptable fillers that may be particularly used for coating the peptides include, without limitation, talc, microcrystalline cellulose (e.g., Avicel PH101 or Celphere CP-305), powdered cellulose, dextrates, kaolin, mannitol, silicic acid, sorbitol, starch, pre-gelatinized starch, lactose, glucose, fructose, galactose, trehalose, sucrose, maltose, isomalt, dibasic calcium phosphate, raffinose, maltitol, melezitose, stachyose, lactitol, palatinite, xylitol, mannitol, myoinositol, and mixtures thereof.

As used herein, the term "additives" refers to any pharmaceutically acceptable additive. Pharmaceutically acceptable additives include, without limitation, disintegrants, dispersing additives, lubricants, glidants, antioxidants, coating additives, diluents, surfactants, flavoring additives, humectants, absorption promoting additives, controlled release additives, anti-caking additives, anti-microbial agents (e.g., preservatives), colorants, desiccants, plasticizers and dyes. As used herein, an "excipient" is any pharmaceutically acceptable additive, filler, binder or agent.

Compositions of the present invention may also optionally include other therapeutic ingredients, anti-caking agents, preservatives, sweetening agents, colorants, flavors, desiccants, plasticizers, dyes, glidants, anti-adherents, anti-static agents, surfactants (wetting agents), anti-oxidants, film-coating agents, and the like. Any such optional ingredient must be compatible with the compound described herein to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

The compositions can include, for example, various additional solvents, dispersants, coatings, absorption promoting additives, controlled release additives, and one or more inert additives (which include, for example, starches, polyols, granulating additives, microcrystalline cellulose, diluents, lubricants, binders, disintegrating additives, and the like), etc. If desired, tablet dosages of the disclosed compositions may be coated by standard aqueous or non-aqueous techniques. Compositions can also include, for example, anti-caking additives, preservatives, sweetening additives, colorants, flavors, desiccants, plasticizers, dyes, and the like.

Suitable disintegrants include, for example, agar-agar, calcium carbonate, microcrystalline cellulose, croscarmellose sodium, crospovidone, povidone, polacrilin potassium, sodium starch glycolate, potato or tapioca starch, other starches, pre-gelatinized starch, clays, other algins, other celluloses, gums, and mixtures thereof.

Suitable lubricants include, for example, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Evonik Degussa Co., Plano, Tex. USA), a pyrogenic silicon dioxide (CAB-O-SIL, Cabot Co., Boston, Mass. USA), and mixtures thereof.

Suitable glidants include, for example, leucine, colloidal silicon dioxide, magnesium trisilicate, powdered cellulose, starch, talc, and tribasic calcium phosphate.

Suitable anti-caking additives include, for example, calcium silicate, magnesium silicate, silicon dioxide, colloidal silicon dioxide, talc, and mixtures thereof.

Suitable anti-microbial additives that may be used, e.g., as a preservative for the peptides compositions, include, for example, benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, and mixtures thereof.

Suitable antioxidants include, for example, BHA (butylated hydroxyanisole), BHT (butylated hydroxytoluene), vitamin E, propyl gallate, ascorbic acid and salts or esters thereof, tocopherol and esters thereof, alpha-lipoic acid and beta-carotene.

Suitable coating additives include, for example, sodium carboxymethyl cellulose, cellulose acetate phthalate, ethylcellulose, gelatin, pharmaceutical glaze, hydroxypropyl cellulose, hydroxypropyl methylcellulose, hydroxypropyl methyl cellulose phthalate, methylcellulose, polyethylene glycol, polyvinyl acetate phthalate, shellac, sucrose, titanium dioxide, carnauba wax, microcrystalline wax, and mixtures thereof. Suitable protective coatings include Aquacoaf (e.g., Aquacoat Ethylcellulose Aqueous Dispersion, 15% w/w, FMC Biopolymer, ECD-30), Eudragit (e.g., Eudragit E PO PE-EL, Roehm Pharma Polymers) and Opadry (e.g Opadry AMB dispersion, 20% w/w, Colorcon).

In certain embodiments, suitable additives for the peptides composition include one or more of sucrose, talc, magnesium stearate, crospovidone or BHA.

The compositions of the present invention can also include other excipients, agents, and categories thereof including but not limited to L-histidine, Pluronic®, Poloxamers (such as Lutrol® and Poloxamer 188), ascorbic acid, glutathione, permeability enhancers (e.g., lipids, sodium cholate, acylcarnitine, salicylates, mixed bile salts, fatty acid micelles, chelators, fatty acid, surfactants, medium chain glycerides), protease inhibitors (e.g., soybean trypsin inhibitor, organic acids), pH lowering agents and absorption enhancers effective to promote bioavailability (including but not limited to those described in U.S. Pat. No. 6,086,918 and U.S. Pat. No. 5,912,014), materials for chewable tablets (like dextrose, fructose, lactose monohydrate, lactose and aspartame, lactose and cellulose, maltodextrin, maltose, mannitol, microcrystalline cellulose and guar gum, sorbitol crystalline); parenterals (like mannitol and povidone); plasticizers (like dibutyl sebacate, plasticizers for coatings, polyvinylacetate phthalate); powder lubricants (like glyceryl behenate); soft gelatin capsules (like sorbitol special solution); spheres for coating (like sugar spheres); spheronization agents (like glyceryl behenate and microcrystalline cellulose); suspending/gelling agents (like carrageenan, gellan gum, mannitol, microcrystalline cellulose, povidone, sodium starch glycolate, xanthan gum); sweeteners (like aspartame, aspartame and lactose, dextrose, fructose, honey, maltodextrin, maltose, mannitol, molasses, sorbitol crystalline, sorbitol special solution, sucrose); wet granulation agents (like calcium carbonate, lactose anhydrous, lactose monohydrate, maltodextrin, mannitol, microcrystalline cellulose, povidone, starch), caramel, carboxymethylcellulose sodium, cherry cream flavor and cherry flavor, citric acid anhydrous, citric acid, confectioner's sugar, D&C Red No. 33, D&C Yellow #10 Aluminum Lake, disodium edetate, ethyl alcohol 15%, FD& C Yellow No. 6 aluminum lake, FD&C Blue #1 Aluminum Lake, FD&C Blue No. 1, FD&C blue no. 2 aluminum lake, FD&C Green No. 3, FD&C Red No. 40, FD&C Yellow No. 6 Aluminum Lake, FD&C Yellow No. 6, FD&C Yellow No. 10, glycerol palmitostearate, glyceryl monostearate, indigo carmine, lecithin, manitol, methyl and propyl parabens, mono ammonium glycyrrhizinate, natural and artificial orange flavor, pharmaceutical glaze, poloxamer 188, Polydextrose, polysorbate 20, polysorbate 80, polyvidone, pregelatinized corn starch, pregelatinized starch, red iron oxide, saccharin sodium, sodium carboxymethyl ether, sodium chloride, sodium citrate, sodium phosphate, strawberry flavor, synthetic black iron oxide, synthetic red iron oxide, titanium dioxide, and white wax.

In some embodiments, there is provided a pharmaceutical composition comprising a peptide described herein and one or more stabilizing agents selected from $Mg^{2+}$, $Ca^{2+}$, $Zn^{2+}$, $Mn^{2+}$, $K^+$, $Na^+$ or $Al^{3+}$, a combination thereof, and/or a sterically hindered primary amine. In further embodiments, the agent is $Mg^{2+}$, $Ca^{2+}$ or $Zn^{2+}$ or a combination thereof. In some embodiments, the cation is provided, without limitation, as magnesium acetate, magnesium chloride, magnesium phosphate, magnesium sulfate, calcium acetate, calcium chloride, calcium phosphate, calcium sulfate, zinc acetate, zinc chloride, zinc phosphate, zinc sulfate, manganese acetate, manganese chloride, manganese phosphate, manganese sulfate, potassium acetate, potassium chloride, potassium phosphate, potassium sulfate, sodium acetate, sodium chloride, sodium phosphate, sodium sulfate, aluminum acetate, aluminum chloride, aluminum phosphate or aluminum sulfate. In further embodiments, the cation is provided as magnesium chloride, calcium chloride, calcium phosphate, calcium sulfate, zinc acetate, manganese chloride, potassium chloride, sodium chloride or aluminum chloride. In other embodiments, the cation is provided as calcium chloride, magnesium chloride or zinc acetate.

In another embodiment, the stabilizing agent is a sterically hindered primary amine. In a further embodiment, the sterically hindered primary amine is an amino acid. In yet a further embodiment, the amino acid is a naturally-occurring amino acid. In a still further embodiment, the naturally-occurring amino acid is selected from the group consisting of: histidine, phenylalanine, alanine, glutamic acid, aspartic acid, glutamine, leucine, methionine, asparagine, tyrosine, threonine, isoleucine, tryptophan, glycine and valine; yet further, the naturally-occurring amino acid is leucine, isoleucine, alanine or methionine. In another embodiment, the sterically hindered primary amine is a non-naturally occurring amino acid (e.g., 1-aminocyclohexane carboxylic acid). In a further embodiment, the sterically hindered primary amine is cyclohexylamine, 2-methylbutylamine or a polymeric amine such as chitosan. In another embodiment, one or more sterically hindered primary amines may be used in a composition.

In some cases, the sterically hindered primary amine has the formula:

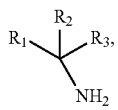

wherein $R_1$, $R_2$ and $R_3$ are independently selected from: H, C(O)OH, $C_1$-$C_6$ alkyl, $C_1$-$C_6$ alkylether, $C_1$-$C_6$ alkylthioether, $C_1$-$C_6$ alkyl carboxylic acid, $C_1$-$C_6$ alkyl carboxylamide and alkylaryl, wherein any group can be singly or multiply substituted with: halogen or amino, and provided that no more than two of $R_1$, $R_2$ and $R_3$ are H. In another embodiment, no more than one of $R_1$, $R_2$ and $R_3$ is H.

In other embodiments, there is provided a pharmaceutical composition comprising a pharmaceutically acceptable carrier, peptide, a cation selected from $Mg^{2+}$, $Ca^{2+}$, $Zn^{2+}$, $Mn^{2+}$, $K^+$, $Na^+$ or $Al^{3+}$, or a mixture thereof, and a sterically hindered primary amine. In one embodiment, the cation is $Mg^{2+}$, $Ca^{2+}$ or $Zn^{2+}$ or a mixture thereof. In a further embodiment, the pharmaceutical composition further comprises a pharmaceutically acceptable binder and/or a pharmaceutically acceptable glidant, lubricant or additive that acts as both a glidant and lubricant and/or an antioxidant. In some embodiments, the pharmaceutical composition is applied to a carrier. In some embodiments, the carrier is a filler.

In some cases the molar ratio of cation:sterically hindered primary amine: peptide in the aqueous solution applied to the carrier is 5-100:5-50:1. In some cases, the molar ratio of cation:sterically hindered primary amine may be equal to or greater than 2:1 (e.g., between 5:1 and 2. Thus, in some cases the molar ratio of cation:sterically hindered primary amine: peptide applied to the carrier is 100:50:1, 100:30:1, 80:40:1, 80:30:1, 80:20:1, 60:30:1, 60:20:1, 50:30:1, 50:20:1, 40:20:1, 20:20:1, 10:10:1, 10:5:1 or 5:10:1. When binder, e.g., methylcellulose, is present in the GC-C agonist peptide solution applied to the carrier it can be present at 0.5%-2.5% by weight (e.g., 0.7%-1.7% or 0.7%-1% or 1.5% or 0.7%).

It has been found that a cation selected from $Mg^{2+}$, $Ca^{2+}$, $Zn^{2+}$, $Mn^{2+}$, $K^+$, $Na^+$ and $Al^{3+}$ is useful for suppressing the formation of an oxidation product of GC-C receptor agonist polypeptides during storage. It has also been found that a sterically hindered primary amine is useful for suppressing the formation of a formaldehyde imine adduct ("formaldehyde imine product") of the GC-C receptor agonist polypeptides during storage. Thus, the GC-C receptor agonist polypeptide formulations comprising a cation selected from $Mg^{2+}$, $Ca^{2+}$, $Zn^{2+}$, $Mn^{2+}$, $K^+$, $Na^+$ or $Al^{3+}$—for example, a divalent cation selected from $Zn^{2+}$, $Mg^{2+}$ and $Ca^{2+}$—and/or a sterically hindered primary amine, such as an amino acid, have a sufficient shelf life (as measured by chromatographic purity and/or by a weight/weight assay) for manufacturing, storing and distributing the drug. Further, while the presence of a sterically hindered amine alone can increase the formation of a hydrolysis product of linaclotide during storage, the combination of a sterically hindered primary amine and a cation, e.g., but not limited to, the combination of leucine and $Ca^{2+}$, suppresses the formation of the hydrolysis product of the GC-C receptor agonist polypeptide as well as the oxidation product of GC-C receptor agonist polypeptide during storage, leading to an even greater overall stability as determined by a weight/weight assay and/or by chromatographic purity.

In a further embodiment, the pharmaceutical composition further comprises a pharmaceutically acceptable binder or additive, and/or a pharmaceutically acceptable glidant, lubricant or additive that acts as both a glidant and lubricant and/or an antioxidant.

Suitable pharmaceutical compositions in accordance with the invention will generally include an amount of the active compound(s) with an acceptable pharmaceutical diluent or excipient, such as a sterile aqueous solution, to give a range of final concentrations, depending on the intended use. The techniques of preparation are generally well known in the art, as exemplified by Remington's Pharmaceutical Sciences (18th Edition, Mack Publishing Company, 1995).

For treatment of gastrointestinal disorders, the peptides described herein are preferably administered orally, e.g., as a tablet, capsule, sachet containing a predetermined amount of the active ingredient pellet, gel, paste, syrup, bolus, electuary, slurry, powder, lyophilized powder, granules, as a solution or a suspension in an aqueous liquid or a non-aqueous liquid; as an oil-in-water liquid emulsion or a water-in-oil liquid emulsion, via a liposomal formulation (see, e.g., EP 736299) or in some other form. Orally administered compositions can include binders, lubricants, inert diluents, lubricating, surface active or dispersing agents, flavoring agents, and humectants. Orally administered formulations such as tablets may optionally be coated or scored and may be formulated so as to provide sustained, delayed or controlled release of the active ingredient therein. The peptides can be co-administered with other agents used to treat gastrointestinal disorders including but not limited to the agents described herein.

In another aspect, suitable pharmaceutical compositions may comprise one or more other therapeutic agents. Such therapeutic agents include, without limitation, analgesic agents; anti-secretory agents, including proton pump inhibitors, acid pump antagonists, H2 receptor antagonists; PDE5 inhibitors; GABA-B antagonists; bile acid sequestrants; prokinetic and promotility agents; antidepressants; antibiotics; antiemetics; and mucosal-protecting agents.

Methods of Treatment

In some embodiments of the invention, a method of treatment is provided for gastrointestinal disorders.

In some embodiments, a method of treatment is provided for colon cancer, inflammatory disorder, obesity, congestive heart failure, benign prostatic hyperplasia (BPH), pain, salt retention, fluid retention, increasing gastrointestinal motility, or decreasing gastrointestinal or visceral pain.

In some embodiments, the gastrointestinal disorder is an upper GI disorder. In a further embodiment, the disorder is GP, post-operative gastric ileus, a functional esophageal disorder, a functional gastroduodenal disorder, gastroesophageal reflux disease (GERD), celiac disease, mucositis, or a duodenal or stomach ulcer.

In some embodiments, the gastrointestinal disorder is gastrointestinal motility disorder, irritable bowel syndrome, constipation predominant irritable bowel syndrome, chronic constipation, a functional gastrointestinal disorder, gastroesophageal reflux disease, duodenogastric reflux, functional heartburn, dyspepsia, functional dyspepsia, nonulcer dyspepsia, gastroparesis, chronic intestinal pseudo-obstruction, diverticulitis, or colonic pseudo-obstruction.

In some embodiments, the gastrointestinal disorder is GP. In further embodiments, the GP is idiopathic, diabetic or post-surgical GP.

In some embodiments, the gastrointestinal disorder is post-operative gastric ileus.

In some embodiments, the gastrointestinal disorder is a functional esophageal disorder.

In some embodiments, the functional esophageal disorder is functional heartburn, functional chest pain of presumed esophageal origin, functional dysphagia or globus.

In some embodiments, the gastrointestinal disorder is a functional gastroduodenal disorder.

In some embodiments, the functional gastroduodenal disorder is FD, a belching disorder, a nausea or vomiting disorder, or rumination syndrome. In a further embodiment, the functional gastroduodenal disorder is FD. In some embodiments, the FD is postprandial distress syndrome or epigastric pain syndrome. In some embodiments, the belching disorder is aerophagia or unspecified excessive belching. In some embodiments, the nausea or vomiting disorder is chronic idiopathic nausea, functional vomiting or cyclic vomiting syndrome.

In some embodiments, the gastrointestinal disorder is gastroesophageal reflux disease (GERD).

In some embodiments, the gastrointestinal disorder is celiac disease. In some embodiments, the gastrointestinal disorder is mucositis. In some embodiments, the gastrointestinal disorder is a duodenal or stomach ulcer.

The peptides and agonists described herein can be used alone or in combination therapy for the treatment, prevention or reduction of visceral pain associated with a upper gastrointestinal disorder or pain associated with another disorder as described herein.

The GC-C receptor agonists described herein can be administered in combination with other agents. For example, the peptides can be administered with an analgesic peptide or compound. The analgesic peptide or compound can be covalently attached to a peptide described herein or it can be a separate agent that is administered together with or sequentially with a peptide described herein in a combination therapy. The GC-C receptor agonists described herein may also be administered in combination with other agents used to treat upper GI disorders including antidepressants, promotility or prokinetic agents, antiemetics, antibiotics, proton pump inhibitors, acid blockers (e.g., histamine H2 receptor antagonists), acid pump antagonists, PDE5 inhibitors, GABA-B agonists, bile acid sequestrants, and mucosal protecting agents.

In some embodiments, useful analgesic agents that may be used with the peptides described herein include Ca channel blockers (e.g., ziconotide), 5HT receptor antagonists (e.g., 5HT3, 5HT4 and 5HT1 receptor antagonists), 5HT4 agonists (e.g., tegaserod (Zelnorm®), mosapride, metoclopramide, zacopride, cisapride, renzapride, benzimidazolone derivatives such as BIMU 1 and BIMU 8, and lirexapride), 5HT1 agonists (e.g., sumatriptan and buspirone), opioid receptor agonists (e.g., loperamide, fedotozine, enkephalin pentapeptide, morphine, diphenyloxylate, frakefamide, trimebutine and fentanyl), CCK receptor agonists (e.g., loxiglumide and dexloxiglumide), NK1 receptor antagonists (e.g., aprepitant, vofopitant, ezlopitant, R-673 (Hoffmann-La Roche Ltd), SR-48968 and SR-14033, (Sanofi Synthelabo), CP-122,721 (Pfizer, Inc.), GW679769 (Glaxo Smith Kline) and TAK-637 (Takeda/Abbot)), NK2 receptor antagonists (e.g., nepadutant, saredutant, GW597599 (Glaxo Smith Kline), SR-144190 (Sanofi-Synthelabo) and UK-290795 (Pfizer Inc)), NK3 receptor antagonists (e.g., osanetant (SR-142801; Sanofi-Synthelabo), SR-241586 and talnetant), norepinephrine-serotonin reuptake inhibitors (NSRI) (e.g., milnacipran), vanilloid and cannabanoid receptor agonists, sialorphin and sialorphin-related peptides. Analgesic agents in the various classes are described in the literature.

In some embodiments, one or more other therapeutic agents may be used in combination with the peptides described herein. Such agents include antidepressants, promotility or prokinetic agents, antiemetics, antibiotics, proton pump inhibitors, acid blockers (e.g., histamine H2 receptor antagonists), acid pump antagonists, PDE5 inhibitors, GABA-B agonists, bile acid sequestrants, and mucosal protecting agents.

Examples of antidepressants include, without limitation, tricyclic antidepressants such as amitriptyline (Elavil®), desipramine (Norpramin®), imipramine (Tofranil®), amoxapine (Asendin®), nortriptyline; the selective serotonin reuptake inhibitors (SSRI's) such as paroxetine (Paxil®), fluoxetine (Prozac®), sertraline (Zoloft®), and citralopram (Celexa®); and others such as doxepin (Sinequan®) and trazodone (Desyrel®).

Examples of promotility and prokinetic agents include, without limitation, itopride, octreotide, bethanechol, metoclopramide (Reglan®), domperidone (Motilium®), erythromycin (and derivatives thereof) and cisapride (Propulsid®). An example of antiemetics includes, without limitation, prochlorperazine.

Examples of antibiotics that may be used include those that may be used to treat *Heliobacter pylori* infections, such as amoxicillin, tetracycline, metronidazole, or clarithromycin. Other antibiotics such as erythromycin and derivatives thereof may also be used in combination with the peptides described herein.

Examples of proton pump inhibitors include, without limitation, omeprazole (Prilosec®), esomeprazole (Nexium®), lansoprazole (Prevacid®), pantoprazole (Protonix®) and rabeprazole (Aciphex®). Examples of H2 receptor blockers include, without limitation, including cimetidine, ranitidine, famotidine and nizatidine. Examples of acid pump antagonists include, without limitation, revaprazan, CS-526 (J. Pharmacol. Exp. Ther. (2007) 323:308-317), PF-03716556 (J. Pharmacol. Exp. Ther. (2009) 328(2):671-9), and YH1885 (Drug Metab. Dispos. (2001) 29(1):54-9).

Examples of PDE5 inhibitors include, without limitation, avanafil, lodenafil, mirodenafil, sildenafil citrate, tadalafil, vardenafil and udenafil. GABA-B agonists include, without limitation, baclofen and XP 19986 (CAS Registry No. 847353-30-4). Examples of bile acid sequestrants include, without limitation, GT102-279, cholestyramine, colesevelam, colesevelam hydrochloride, ursodeoxycholic acid, colestipol, colestilan, sevelamer, polydiallylamine cross-linked with epichlorohydrin, dialkylaminoalkyl derivatives of a cross-linked dextran, and N-(cycloalkyl)alkylamines. Examples of mucosal protecting agents include, without limitation, sucralfate (Carafate), teprenone, polaprezinc, cetraxate and bismuth subsalicyclate.

Combination therapy can be achieved by administering two or more agents, e.g., a GC-C receptor agonist described herein and another therapeutic peptide or compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

Dosage

The pharmaceutical compositions and peptides of the invention are administered in therapeutically effective amounts. A therapeutically effective amount is an amount sufficient to treat and/or prevent or ameliorate a gastrointestinal disorder, colon cancer, an inflammatory disorder, obesity, congestive heart failure, benign prostatic hyperplasia (BPH), pain, salt retention or fluid retention. In certain aspects of the invention a therapeutically effective amount is an amount sufficient to ameliorate or lessen any symptoms associated with a disorder including gastrointestinal disorder, colon cancer, an inflammatory disorder, obesity, congestive heart failure, benign prostatic hyperplasia (BPH), pain, salt retention or fluid retention.

The dose range for adult humans may be generally from 5 µg to 100 mg/day orally of the GC-C peptide agonist described herein. Tablets, capsules, or other forms of presentation provided in discrete units may conveniently contain an amount of compound described herein which is effective at such dosage or as a multiple of the same, for instance, units containing 25 µg to 2 mg or around 100 µg to 1 mg. The precise amount of compound prescribed to a patient will be the responsibility of the attendant physician. However, the dose employed will depend on a number of factors, including the age and sex of the patient, the precise disorder being treated, and its severity.

In various embodiments, the dosage unit is administered with food at anytime of the day, without food at anytime of the day, with food after an overnight fast (e.g. with breakfast), at bedtime after a low fat snack. In one particular embodiment, the dosage unit is administered prior to or subsequent to food consumption (e.g., a meal). In a further embodiment, the dosage unit is administered approximately 15 minutes to 1 hour prior to food consumption. In various embodiments, the dosage unit is administered once a day, twice a day, three times a day, four times a day, five times a day or six times a day. In certain embodiments the dosage unit and daily dose are equivalent.

In combination therapy embodiments of the present invention, the precise amount of each of the two or more active ingredients in a dosage unit will depend on the desired dosage of each component. Thus, it can be useful to create a dosage unit that will. when administered according to a particular dosage schedule (e.g., a. dosage schedule specifying a certain number of units and a particular timing for administration), deliver the same dosage of each component as would be administered if the patient was being treated with only a single component. in other circumstances, it might be desirable to create a dosage unit that will deliver a dosage of one or more components that is less than that which would be administered if the patient was being treated only with a single component. Finally, it might be desirable to create a dosage unit that will deliver a dosage of one or more components that is greater than that which would be administered if the patient was being treated only with a single component.

The pharmaceutical composition can include additional ingredients including but not limited to the active ingredients and excipients described herein. In certain embodiments, one or more therapeutic agents of the dosage unit may exist in an extended or control release formulation and additional therapeutic agents may not exist in extended release formulation. For example, a peptide or agonist described herein may exist in a controlled release formulation or extended release formulation in the same dosage unit with another agent that may or may not be in either a controlled release or extended release formulation. Thus, in certain embodiments. it may be desirable to provide for the immediate release of one or more of the agents described herein, and the controlled release of one or more other agents.

The present invention has been described with reference to certain exemplary embodiments thereof. However, it will be readily apparent to those skilled in the art that it is possible to embody the invention in specific forms other than those of the exemplary embodiments described above. This may be done without departing from the spirit of the invention. The exemplary embodiments are merely illustrative and should not be considered restrictive in any way. The scope of the invention is defined by the appended claims and their equivalents, rather than by the preceding description.

EXAMPLES

The GC-C agonist peptides or pharmaceutically acceptable salts thereof as described herein are prepared by solid phase chemical synthesis and natural folding (air oxidation) by American Peptide Company (Sunnyvale, Calif.).

Example 1

Alkaline and Acid Phosphatase Effects on Peptide Substrates

For the alkaline phosphatase reactions, peptide stocks are prepared at 1 mg/mL in 0.1 M Tris-HCl pH 8, which were stored at −20° C. until assays are conducted. For the acid phosphatase reactions, peptide stocks are prepared at 1 mg/mL in 50 mM sodium phosphate pH 6, which was stored at −20° C. until assays are conducted.

Alkaline Phosphatase Reaction

Calf intestinal alkaline phosphatase (CIP) is obtained from New England BioLabs, Ipswich, Mass. Cat # M0290S. The CIP reaction solution is prepared by dilution with buffer (50 mM KCl, 10 mM Tris-HCl pH 8, 1 mM $MgCl_2$, 50% glycerol) to 0.5 units/μL. The alkaline phosphatase reaction solutions are assembled in 20 μL quantities containing:

2 μL 10×CIP buffer (1M NaCl, 500 mM Tris-HCl pH 8, 100 mM $MgCl_2$)
2 μL peptide stock (1 mg/mL)
12 μL $H_2O$
4 μL alkaline phosphatase (0, 0.5 or 2 units)

The reaction solutions are mixed gently and incubated for 90 minutes at 37° C. These reaction solutions were stored at −20° C. until analysis. For analysis, the reaction solutions are diluted from 7.5 μL of CIP treated peptide to 50 μL with 0.1% formic acid in water to a final concentration of 10 μM. The final solution of 20 μL is then analyzed by LCMS. Control reactions are assembled for enzyme activity containing 10 mM p-nitrophenylphosphate in place of peptide. After incubation, the reactions are diluted with 0.1 mL of 100 mM borate buffer pH 9 and read at the absorbance of 405 nm to monitor p-nitrophenol appearance.

Acid Phosphatase Reactions

Potato acid phosphatase (PoAP) is obtained from Sigma, St. Louis, Miss. Cat #P1146 and human prostate acid phosphatase (HuPrAP) is obtained from MP Biochemicals, Solon, Ohio. Cat #153872. The acid phosphatases are dissolved to provide a solution containing 0.5 units AP/μL using 50 mM sodium acetate pH 5, 0.2 mM $MgCl_2$. The acid phosphatase reactions are assembled in 20 μL quantities containing:

2 μL 10× acid phosphatase buffer (500 mM sodium acetate pH 5, 2 mM $MgCl_2$)
2 μL peptide stock (1 mg/mL)
12 μL $H_2O$
4 μL acid phosphatase (0.5 or 2 units)

The reaction solutions are mixed gently and incubated for 90 minutes at 37° C. The reaction solutions are stored at −20° C. for later analysis. For analysis, 7.5 pt acid phosphatase reactions are diluted to 50 μL with 0.1% formic acid in water to a final concentration of 10 μM. The final reactions of 20 μL are analyzed by LCMS. The control reactions for enzyme activity are assembled and diluted to 10 mM p-nitrophenylphosphate in place of peptide. After incubation, the reactions are diluted with 0.1 mL of 100 mM borate buffer pH 9 and read at the absorbance of 405 nm to monitor p-nitrophenol appearance.

Example 2 cGMP Accumulation in T84 Cells for Analysis of GC-C Activity

The ability of peptides, variant peptides and other compounds to bind to and activate the intestinal GC-C receptor can be tested using the T84 human colon carcinoma cell line (American Type Culture Collection (Bethesda, Md.)).

For the cGMP assay, $4.5 \times 10^5$ cells/mL of T84 cells are grown overnight in 24 well tissue culture plates. On the next day, the T84 cells are washed twice with 1 mL of DMEM+20 mM MES (pH 5) or DMEM+50 mM sodium bicarbonate (pH8) in which these buffers did not contain serum. After the second wash, the cells are incubated with 450 μL of 1 mM isobutylmethylxanthine (IBMX) in either the pH 5 or pH 8 buffers for 10 minutes at 37° C. to inhibit any phosphodiesterase activity. The peptides are then diluted in either pH 5 or pH 8 buffer to a 10× concentration. The peptide solution of 50 μL is diluted to a final volume of 500 μL with the T84 cells, bringing each peptide concentration to 1×. An eleven point curve analysis is conducted for each peptide, with final peptide concentrations tested in each assay, in nM: 10000, 3000, 1000, 300, 100, 30, 10, 3, 1, 0.3, 0.1.

There is no peptide control used to determine endogenous levels of cGMP. Peptides are incubated for 30 minutes at 37° C. After 30 minutes, the supernatants are removed and the cells are lysed with 0.1 M HCl. The cells are lysed for 30 minutes on ice. After 30 minutes, lysates are pipetted off and placed into a 96 well HPLC plate and spun at 10,000×g for 10 minutes to remove any cell debris. Supernatants from the previous spin are removed and placed into a fresh 96 well HPLC plate. Samples are diluted with an equal volume of 1 M ammonium acetate (pH 7) to neutralize samples for better chromatography. A 2× cGMP standard curve is prepared in 0.1 M HCl and then diluted with an equal volume of 1 M ammonium acetate, with the following final concentrations in nM: 1024, 512, 256, 128, 64, 32, 16, 8, 4, 2, 1.

cGMP concentrations are determined from each sample using the LC/MS conditions in Table 4 and a calculated standard curve. $EC_{50}$ values are calculated from concentration-response curves generated with GraphPad Prism Software.

The ability of the peptides of the invention and their dephosphorylated forms to stimulate cGMP synthesis in human T84 cells at pH 5 is tested by incubating the cells with the peptides followed by determination of the accumulated intracellular cGMP by LC-MS.

Example 3

Competitive Radioligand-Binding on T84 Cells

Intact human T84 cells from the American Type Culture Collection (ATCC; Manassas, Va.) are used for competitive radioligand-binding experiments. The T84 cells are grown in monolayers on T-150 plastic flasks to 60-70% confluency in Dulbecco's Modified Eagle Medium: Ham's F-12 50/50 media (DMEM/F12)+5% fetal bovine serum (FBS). The cells are harvested by gentle scraping with a cell scraper and cells collected by centrifuge at 2000 g for 10 minutes at 4° C. The cells are washed twice by resuspending gently in phosphate buffered saline (PBS) and collecting them by centrifugation as above.

$[^{125}I]$-STp radioligand is prepared by dissolving one hundred micrograms (100 μg) of NTFYCCELCCNPACAGCY [SEQ ID NO: 31] (Enterotoxin STp; Bachem H-6248) in 0.5 mL water and sent to Perkin-Elmer Life and Analytical Sciences (N. Billerica, Mass.) for iodination using the lactoperoxidase method recited in (Marchanolis, J. J., "An enzymic method for the trace iodination of immunoglobulins and other proteins," *Biochem. J.* 1969, 113, 299-305). Perkin-Elmer purified the labeled tracer by HPLC using a Waters C-18 μBondapak column (25 cm) previously equilibrated with 10 mM ammonium acetate pH 5.8. A gradient from 0 to 25% acetonitrile is applied to the column in 60 min, followed by isocratic elution at 25% acetonitrile for another 20 mM. This method separates two monoiodinated forms from each other and from unlabeled precursor. The second monoiodinated peak (Peak 2) which elutes after 64 min and corresponds to iodination of the fourth tyrosine, is used as the labeled tracer in the assay. The labeled tracer has a specific activity of 2200 Ci/mmol. Upon arrival, tracer is stored in aliquots at −20° C.

The binding reactions are assembled in duplicate in 0.2 mL containing: $2.5 \times 10^5$ T84 cells (0.25 mg protein), 200,000 cpm [$^{125}$I]-STp (41 fmol, 200 pM), 0.1 to 3,000 nM competitor, and 0.5% bovine serum albumin (BSA). The binding assays are conducted at pH 5.0 in DMEM/20 mM 2-(N-morpholino) ethanesulfonic acid (MES). The binding assays at pH 8.0 are performed in DMEM/20 mM N-2-Hydroxyethylpiperazine-N'-2-Ethane Sulfonic Acid (HEPES)/50 mM sodium bicarbonate. The control reactions do not contain a competitor (total) or no cells.

The buffer solutions are prepared first, then protease-free BSA is added to 0.5%. The radioligand is added to a final concentration of 0.001 µCi/µL. Preparation of competitor peptide stock solutions are made by dissolving peptides to 1 mg/mL in 50 mM sodium phosphate pH 6.0. Concentrations are calculated from the peptide molecular weight provided in the Certificate of Analysis. Competitor dilutions are made in 50 mM sodium phosphate pH 6.0 that contains 20 times the final concentration of peptide to be tested in the binding reaction (20× competitor).

The binding reactions are assembled in the following order:
  i. Radioligand and BSA in buffer solution.
  ii. 10 µL of 20× competitor.
  iii. T84 cells.

The binding reactions are mixed gently and incubated at 37° C. for 1 h. Separation of membrane-bound from free radioligand is conducted by applying the binding reactions to 2.5 cm Whatman GF/C glass-fiber filters (pretreated with 1% polyvinylpyrrolidone in PBS) using vacuum filtration. The filters are rinsed twice with 5 mL ice-cold PBS buffer and measurements of the trapped radioligand is conducted in a scintillation counter. The determination of specific binding is made by subtracting the bound radioactivity from a reaction that contains excess competitor (1 µM) from the bound radioactivity of each sample. The generation of competitive radioligand-binding curves are made using GraphPad Prism (GraphPad Software, San Diego, Calif.) and the data is analyzed with nonlinear regression to calculate the concentration of competitor that resulted in 50% radioligand bound ($IC_{50}$). The apparent dissociation equilibrium constant ($K_i$) for each competitor is obtained, from the $IC_{50}$ values and a previously determined estimate of the dissociation constant for the radioligand, $K_d \approx 15$ nM, using the method of (Cheng and Prusoff, (1973) Biochem. Pharmacol. 22(23) 3099-3108).

Example 4

Gastrointestinal Transit in Mice

In order to determine whether a test compound or a peptide, increases the rate of gastrointestinal transit, the test compound can be tested in the murine gastrointestinal transit (GIT) assay (Moon et al. *Infection and Immunity* 25:127, 1979). In this assay, charcoal, which can be readily visualized in the gastrointestinal tract is administered to mice after the administration of a test compound. The distance traveled by the charcoal is measured and expressed as a percentage of the total length of the colon.

The purpose of the assay is to test the effect of the guanylate cyclase C agonist peptides on in vivo gastrointestinal transit in mice. Orally-dosed guanylate cyclase C agonists have been demonstrated to increase the % Distance Travelled by a charcoal meal in mice.

For the assay, female CD-1 mice (n=10 per group) weighing 25-30 g are fasted overnight and given access to water ad libitum. Activated charcoal (20 g; 100 mesh; Sigma cat#242276) is suspended in 200 mL gum arabic (100 mg/mL), and stirred for at least one hour. Test peptides are prepared in a 20 mM Tris pH 6.9 vehicle.

Test peptide and vehicle are administered in 200 µL doses by oral gavage. Seven minutes after dosing the test peptides, 200 µL of the charcoal/gum arabic suspension is dosed by oral gavage. After 15 minutes, mice are sacrificed by $CO_2$ overdose. The gastrointestinal tract is removed from the esophagus to the caecum. The total length of the small intestine is measured from the pyloric junction to the ileocaecal junction. The distance travelled by the charcoal is measured from the pyloric junction to the charcoal front. The Distance Travelled (%) is determined as (distance travelled by charcoal/total length of the small intestine)×100. Data are entered into the GraphPad Prism software program and analyzed by ANOVA using a Bonferroni multiple comparison test post-hoc. Plots of data and $ED_{50}$ are also determined using the GraphPad Prism software package.

The dose-dependent effects of acute doses of the peptides of the invention and the dephosphorylated forms the peptides of the invention on GI transit are determined in female CD mice. The distance traveled by the charcoal front after seven minutes, expressed as a percent of total length of small intestine is used to calculate $ED_{50}$ values.

Example 5

Fluid Secretion in Rat Intestinal Loops

The effect of GC-C agonist peptides on secretion are studied by injecting GC-C agonist peptides described herein directly into an isolated loop in wild-type rats.

Loops are isolated by surgically ligating three loops in the small intestine of the rat. The methodology for ligated loop formation is similar to that described in (London et al., 1997, Am J Physiol, p.G 93-105). The loops are roughly centered and at lengths of 1-3 cm. The loops are injected with 200 µl of either peptide/GC-C agonist (0.1-5 µg) or vehicle (20 mM Tris, pH 7.5 or Krebs Ringer, 10 mM Glucose, HEPES buffer (KRGH)). Following a recovery time of up to 90 minutes the loops are excised. Weights are recorded for each loop before and after removal of the fluid contained therein. The length of each loop is also recorded. A weight to length ratio (W/L) for each loop is calculated to determine the effects of the GC-C agonist peptide described herein on secretion. Loop fluid volume is also determined.

Example 6

In Vitro Metabolism in Mouse Jejunum Loop Fluid

The purpose of this study is to determine the stability of phosphorylated peptides in mouse jejunal loop fluid. Phosphorylated and isotopically labeled peptides according to the invention are used in the study. The isotopically labeled peptides are synthesized with $^{13}$C, $^{15}$N-labeled alanine and leucine (i.e., with a sequence CCpS[$^{13}$C$_6$, $^{15}$N]LCCNP[$^{13}$C$_6$, $^{15}$N]ACTGC).

Each peptide is synthesized by American Peptide Company, Inc., and is stored desiccated at −20° C. A 1 mg/mL solution for each of the non-labeled peptides is prepared in 1 M tris(hydroxymethyl)aminomethane hydrochloride (Tris-HCl), pH 8 just prior to conducting the mouse intestinal loop fluid assay. A 500 ng/mL solution of $^{13}$C, $^{15}$N-labeled peptides is prepared in 0.1% formic acid in water and is utilized to dilute the jejunum samples for post-assay LC-MS/MS analysis.

To study the metabolism of phosphorylated and dephosphorylated peptides according to the invention in vitro, the peptides are incubated in mouse jejunum fluid extracted from loops ligated in the small intestine of mice. To collect the fluid, mice are fasted overnight with full access to water. They are then anesthetized with isofluorane for surgery and subjected to laparotomy in which the small intestine is exteriorized. Jejunum loops of 3 to 4 cm in length are made with sutures starting at 7 cm from the pyloric sphincter of the stomach. Once the loops are formed, they are injected with 200 µL of phosphate buffered saline (PBS) buffer (10 mM, pH 7.4). The abdominal wall and skin of the animals are then sutured, and the animals are allowed to recover for 30 minutes. Following recovery, the animals are sacrificed, the loops are then excised and the fluid inside is recovered and stored at −80° C. until use.

For each peptide, 25 µL of the 1 mg/mL peptide stock solution is added to 25 µl of 1 M Tris-HCl and 25 µL of 10× calf intestinal phosphatase (CIP) buffer containing 500 mM Tris-HCl, 1 M sodium chloride (NaCl), 0.1 mM magnesium chloride ($MgCl_2$), pH 8. The reactions are initiated by adding 175 µL of the mouse jejunum loop fluid or 175 µL of the 1 M Tris-HCl pH8 buffer for the control reactions. The final concentration of each peptide is 100 µg/mL. The reactions are continuously mixed and maintained at 37° C. on a plate shaker. At 0, 2, 5, 10, 20, 30, 60, 90 and 120 minutes after adding the mouse intestinal loop fluid, a 25 µL aliquot is taken and added to 25 µL of 4° C. 12% trichloroacetic acid to stop the reaction. An additional 200 µL of 0.1% formic acid in water is added to these reactions for dilution purposes. These samples are then further diluted by taking 20 µL of each sample and adding it to 480 µL of 0.1% formic acid in water containing 500 ng/mL of the internal standard.

The concentration of peptides in the samples is measured by LC-MS/MS. All samples are analyzed using an Applied Biosystems/MDS SCIEX API 4000 triple quadrupole mass spectrometer equipped with a high-performance liquid chromatography (HPLC) system. The mass spectrometer is operated in multiple reaction monitoring (MRM) mode, with resolution set to 1.2 Da.

The LC-MS/MS data are processed using Analyst version 1.4.2 software (Applied Biosystems/MDS SCIEX). The peak area ratio (ratio of analyte peak area to internal standard peak area) is used to calculate the percent remaining of each peptide.

The percent remaining of peptides at the nine time points is measured during the 120 minute incubation in mouse jejunum fluid and in the control reaction (1 M Tris-HCl) at 37° C. After the incubation in the mouse jejunal loop fluid, only low percentage of the peptides of the invention remained after 120 minutes. The metabolite, dephosphorylated peptide, is formed in this reaction and increases in concentration for the first 20 minutes then shows a slow decrease for the remaining time. In the control reaction, the peptides of the invention are not metabolized and no dephosphorylated metabolite is formed. After the incubation in the mouse jejunum fluid, only small percentage of the dephosphorylated peptide remains after 120 minutes. In contrast, dephosphorylated peptide is not metabolized in the control reaction. Certain peptides of the invention are rapidly metabolized and are not detected after 90 minutes in the mouse jejunum fluid. In the control reaction, these peptides are not metabolized.

Example 7

Liquid Gastric Emptying in Strepozotocin (STZ)-Induced Diabetic Rats

The effect of peptides 2 and 3 administered via oral gavage on liquid gastric emptying (LGE) in strepozotocin (STZ)-induced diabetic rats is studied.

Adult male rats (Sprague-Dawley; n=60) weighing ~300 g (supplied by Taconic) are housed in controlled conditions of room temperature (22° C.) and light (12:12 h light-dark cycle) with free access to food and water. Following a one-week acclimation period, the STZ protocol for inducing type I diabetes is initiated.

To induce type I diabetes in animals in the STZ experimental group (n=50), a daily regimen of intraperitoneal injections of STZ (20 mg/kg) contained in citrate buffer is administered for 5 days. A control group receives an equal volume of the vehicle (n=10) over the same injection schedule. All animals are given 9 weeks to develop diabetes/recover from the injections. Blood glucose levels are monitored post 5-day STZ injection at day 0 (i.e., on day 6) and at week 1, 2 and 10 (i.e., beginning of week 10—the day of the experiment). Blood samples are taken from the tail vein, except on the day of the Liquid Gastric Emptying (LGE) experiment (beginning of week 10), in which blood is taken directly from the heart.

The LGE procedure involved 6 groups (n=10/group) of which five groups are diabetic and one group is non-diabetic. Prior to the LGE experiment, food is withheld overnight, whereas water is withheld 2 hr before starting the gastric emptying procedure.

Peptides are dissolved separately in a vehicle of 20% sucrose solution containing 0.1 mg/ml phenol red. The drug doses for the compounds employed are (in mg/kg): 0.1, 0.3 and 1.0. To test their effect on LGE, a 0.5 ml volume of the drug solution is then delivered via an 18-gage gavage needle (6 cm in length) into the stomach either of diabetic animals or of control animals. Each animal in the diabetic experimental groups receives a single drug dose of a peptide. In the non-diabetic group, animals are administered a similar volume of only the vehicle solution. All animals are then allowed 15 minutes for gastric emptying to occur, after which they are euthanized with isoflurane.

Following euthanasia, via a laparotomy, the stomach is accessed and ligated in each animal at the lower esophageal sphincter and the pyloric sphincter. Next, the heart is exposed through an incision in the diaphragm, a blood sample is taken and glucose level is assessed with a glucometer. The stomach is then excised from the animal and stored overnight in a 10 ml tube containing 95% ethanol. Next, the tissue is homogenized, centrifuged (twice at 40,000 g for 30 min) and the supernatant is tested for absorbance in a spectrophotometer (BioMate 3, Thermospectronic, Inc.) at 410 nm wavelength. Results are compared to a "zero value" derived from administration of the sucrose/phenol red solution to the stomach of an animal that is immediately sacrificed and its stomach removed to determine the "percent retained" for each group.

The fasting glucose levels of both the STZ diabetic animals and the control animals are >300 mg/dL on the day of the gastric emptying experiment. The overall weights of the STZ diabetic animals are appreciably less than the non-diabetic animals on the day of the experiment. Both groups of animals start at approximately 300 g at the time of treatment with STZ; the non-treated ammonals gain, on average, 130 g over the 10 weeks prior to LGE treatment, while the STZ diabetic animals stay at a constant weight until fasting.

The experiments are done to determine the effect of peptides of the invention on LGE in STZ-induced diabetic rats (9 wk). Few different doses of the peptides are evaluated.

Example 8

Evaluation of the Anti-Nociceptive Effects of Increasing Doses of the Peptides of the Invention on Basal and Post-Inflammatory Colorectal Hypersensitivity to Distension in Male Wistar Rats The objective of this study is to evaluate the effects of low increasing doses of the peptides of the invention on basal and post-inflammatory 2,4,6-trinitrobenzene sulfonic acid (TNBS)-induced colorectal hypersensitivity to distension in male Wistar rats.

Materials and Methods

Peptides are prepared at the appropriate concentrations in a 20 mM Tris HCl, pH 6.85 vehicle.

Animals and Surgical Procedures

Male Wistar rats (Janvier S A, Le Genest St Isle, France) weighing 220-250 grams are used in this study. The rats are housed individually in propylene cages and are surgically prepared for electromyography (EMG) according to a protocol described in (Morteau O et al., Science (1994) 39: 1239-1248). Under general anesthesia induced by intraperitoneal (ip) administration of 0.6 mg/kg acepromazine (Calmivet; Vetoquinol, Lure, France) and 120 mg/kg ketamine (Imalgene 1000; Rhone Merieux animals), three pairs of nickel-chromium (NiCr) electrodes are each implanted in the striated muscles of the abdomen. The electrodes are exteriorized on the back of the neck and protected by a glass tube attached to the skin.

EMG recordings are initiated five days after surgery. The electrical activity was recorded with an electromyograph (Mini VIII, Alvar, Paris, France) using a short time constant (0.03 seconds) to remove low-frequency signals (<3 Hz) and a paper speed of 3.6 cm/minute. During the experiment, the number of spike bursts on the EMG recordings that corresponded to abdominal contractions is determined per 5 minute periods.

TNBS Administration

Rats are fasted overnight. Following the fasting period, 2,4,6-trinitrobenzene sulfonic acid (TNBS; 80 mg/kg in 0.3 ml 50% ethanol) is infused intrarectally (ir) through a silicone catheter that is surgically introduced under anesthesia at 4 cm from the anus using the method of Morteau et al. to induce colonic inflammation.

Colorectal Distension Procedure and Colorectal Volume Recordings

Rats are accustomed to polypropylene tunnel devices (diameter: 7 cm; length: 20 cm) during three days (3 h/day) prior to the start of colorectal distension (CRD) procedures to minimize recording artifacts caused by movement of the animals. The balloon used for distension is 4 cm in length and is prepared from a latex condom fixed on a rigid catheter taken from an embolectomy probe (Fogarty). The balloon is inserted into the rectum at 1 cm from the anus and fixed at the basis of the tail. Isobaric distensions are performed from 0 mmHg to 60 mmHg by connecting the balloon to a computerized barostat. The first distension is performed at a pressure of 15 mmHg, and an increment of 15 mmHg is added at each following step until a maximal pressure of 60 mmHg, with each distension step lasting for a period of 5 min. Colonic pressure and balloon volume are continuously monitored on a potentiometric recorder (L6514, Linseis, Selb, Germany) with a paper speed of 1 cm/minute.

Experimental Design

Basal sensitivity to colorectal distension was established in each group, with distension pressures increasing by 15 mmHg increments as detailed above. Next, each group is individually orally dosed with either peptide or vehicle (20 mM Tris HCl, pH 6.85) one hour prior to colorectal distension. CRD treatments are performed as for the basal measurements. The following day, TNBS (80 mg/kg, ir) is administered as described above. Three days after TNBS administration, rats are treated with either peptide or vehicle (20 mM Tris HCl, pH 6.85) one hour prior to colorectal distension as before. CRD treatments were performed as for the basal measurements.

Example 9

The Effects of the Peptides of the Invention on Basal and Stress-Induced Colorectal Hypersensitivity to Distension in Female Wistar Rats The objective of this study is to evaluate the effects of peptides of the invention on basal and stress-induced colorectal hypersensitivity to distension in female Wistar rats.

Materials and Methods

Peptides are prepared at the appropriate concentrations in a 20 mM Tris HCl, pH 6.85 vehicle. Female Wistar rats (Janvier S A, Le Genest St Isle, France) weighing 220-250 grams are used in this study. Husbandry of the animals and EMG implantation and recording are performed as described. The colorectal distension procedure and intestinal volume recordings are performed as described.

Partial Restraint Stress

Partial restraint stress (PRS), a relatively mild form of stress, is performed as previously described in (Williams et al. American Journal of Physiology (1987) 253: G582-G586). Briefly, rats are lightly anaesthetized with ethyl-ether, and their freeholders, upper forelimbs and thoracic trunk are wrapped in a confining harness of paper tape to restrict, but not to prevent body movement, and placed in their home cages for two hours. PRS was always performed between 10:00 am and 12:00 pm.

Experimental Design

The experimental design of the study includes female Wistar rats (n=10) were orally dosed with either peptide or vehicle (20 mM Tris HCl, pH 6.85), one hour prior to CRD on day 0. The following day, CRD is performed prior to PRS. Next, 1.5 hours after CRD, the animals are subjected to 2 hours of PRS. Animals are orally dosed with either peptide or vehicle 1.25 hours into the 2-hour stress session. Fifteen minutes after PRS, the animals are subjected to CRD. Comparisons of the number of abdominal contractions for each 5-minute period during rectal distension are performed using the non-parametric Wilcoxon test for paired data (same group before and after stress session) or the non-parametric Mann-Whitney test for unpaired data (comparison of vehicle group versus peptide group).

OTHER EMBODIMENTS

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

What is claimed is:

1. A polypeptide comprising the amino acid sequence:
Xaa$_1$-Xaa$_2$-Xaa$_3$-Cys$_4$-Xaa$_5$-Xaa$_6$-Cys$_7$-Xaa$_8$-Xaa$_9$-Xaa$_{10}$-Ala$_{11}$-Cys$_{12}$-Xaa$_{13}$-Xaa$_{14}$-Cys$_{15}$-Xaa$_{16}$-Xaa$_{17}$-Xaa$_{18}$ [SEQ ID NO: 22] wherein
Xaa$_1$ is Gly, Asn, Pro, Gln, Ser, Thr, Ala, Val, Leu, Ile, Met, Phe, Trp, Tyr or is absent;
Xaa$_2$ is Asp, Glu, Gly, His, Asn, Ser, Gln, Thr or is absent;
Xaa$_3$ is Thr, Glu, Asp, or Ser;
Xaa$_5$ is P-Ser, P-Thr, P-homo-Ser, 4-hydroxyvaline phosphate, P-homo-Thr, P-Cys or P-Tyr
Xaa$_6$ is Ile or Leu;
Xaa$_8$ is Val, Ile, Ala, or Leu;
Xaa$_9$ is Asn, Tyr, Phe, or Gln;
Xaa$_{10}$ is Val, Ile, Ala, Leu or Pro;
Xaa$_{13}$ is Ala, Ser or Thr;
Xaa$_{14}$ is Gly or Ala;
Xaa$_{16}$ is Leu, Ile, Phe, Trp, Tyr, or is absent;
Xaa$_{17}$ is Arg, Lys, Ala, Leu, Val, Ile, Ser, Thr, Met, Phe, Trp, Tyr, Asp, Glu, Gln, Asn or is absent; and
Xaa$_{18}$ is Arg, Lys, Ala, Leu, Val, Ile, Ser, Thr, Met, Phe, Trp, Tyr, Asp, Glu, Gln, Asn or is absent.

2. The polypeptide according to claim 1, wherein:
Xaa$_1$ is Gly, Asn, Pro, Gln, Ser, Thr, or is absent;
Xaa$_2$ is Asp, Glu, Gly, His, Asn, Ser, or is absent;
Xaa$_3$ is Thr, Glu, or Asp;
Xaa$_5$ is P-Ser, P-Thr, P-homo-Ser, 4-hydroxyvaline phosphate, P-homo-Thr, P-Cys or P-Tyr
Xaa$_6$ is Ile or Leu;
Xaa$_8$ is Val, Ile, or Ala;
Xaa$_9$ is Asn, Tyr, or Phe;
Xaa$_{10}$ is Val, Ile, or Ala;
Xaa$_{13}$ is Ala or Thr;
Xaa$_{14}$ is Gly;
Xaa$_{16}$ is Leu, Phe, Tyr, or is absent;
Xaa$_{17}$ is Arg, Lys, Ala, Leu, Val, Ile, Ser, Thr, Met, Phe, Trp, Tyr, Asp, Glu, Gln, Asn or is absent; and
Xaa$_{18}$ is Arg, Lys, Ala, Leu, Val, Ile, Ser, Thr, Met, Phe, Trp, Tyr, Asp, Glu, Gln, Asn or is absent.

3. The polypeptide according to claim 2, wherein:
Xaa$_1$ is Pro, Ser, or is absent;
Xaa$_2$ is Gly, His, Asn, Ser, or is absent;
Xaa$_3$ is Thr;
Xaa$_5$ is P-Ser, P-Thr, P-homo-Ser, 4-hydroxyvaline phosphate, P-homo-Thr, P-Cys or P-Tyr
Xaa$_6$ is Ile;
Xaa$_8$ is Ala;
Xaa$_9$ is Tyr or Phe;
Xaa$_{10}$ is Ala;
Xaa$_{13}$ is Ala or Thr;
Xaa$_{14}$ is Gly;
Xaa$_{16}$ is Leu, Phe, Tyr, or is absent;
Xaa$_{17}$ is Arg, Lys, Ala, Leu, Val, Ile, Ser, Thr, Met, Phe, Trp, Tyr, Asp, Glu, Gln, Asn or is absent; and
Xaa$_{18}$ is Arg, Lys, Ala, Leu, Val, Ile, Ser, Thr, Met, Phe, Trp, Tyr, Asp, Glu, Gln, Asn or is absent.

4. The polypeptide according to claim 3, wherein:
Xaa$_1$ is Pro, Ser, or is absent;
Xaa$_2$ is Gly, His, Asn, Ser, or is absent;
Xaa$_3$ is Thr;
Xaa$_5$ is P-Ser, P-Thr, P-homo-Ser, 4-hydroxyvaline phosphate, P-homo-Thr, P-Cys or P-Tyr
Xaa$_6$ is Ile;
Xaa$_8$ is Ala;
Xaa$_9$ is Tyr or Phe;
Xaa$_{10}$ is Ala;
Xaa$_{13}$ is Ala or Thr;
Xaa$_{14}$ is Gly;
Xaa$_{16}$ is Leu, Phe, Tyr, or is absent;
Xaa$_{17}$ is Arg, Lys, Ala, Val, Leu, Ile or is absent; and
Xaa$_{18}$ is Arg, Lys, Ala, Val, Leu, Ile or is absent.

5. The polypeptide according to claim 4, wherein:
Xaa$_1$ is Gly, Asn, Gln, Thr, or is absent;
Xaa$_2$ is Asp, Glu, or is absent;
Xaa$_3$ is Glu or Asp;
Xaa$_5$ is P-Ser, P-Thr, P-homo-Ser, 4-hydroxyvaline phosphate, P-homo-Thr, P-Cys or P-Tyr
Xaa$_6$ is Leu;
Xaa$_8$ is Val or Ile;
Xaa$_9$ is Asn;
Xaa$_{10}$ is Val or Ile;
Xaa$_{13}$ is Thr;
Xaa$_{14}$ is Gly;
Xaa$_{16}$ is Leu, Phe, Tyr, or is absent;
Xaa$_{17}$ is Arg, Lys, Ala, Leu, Val, Ile, Ser, Thr, Met, Phe, Trp, Tyr, Asp, Glu, Gln, Asn or is absent; and
Xaa$_{18}$ is Arg, Lys, Ala, Leu, Val, Ile, Ser, Thr, Met, Phe, Trp, Tyr, Asp, Glu, Gln, Asn or is absent.

6. The polypeptide according to claim 5, wherein:
Xaa$_1$ is Gly, Asn, Gln, Thr, or is absent;
Xaa$_2$ is Asp, Glu, or is absent;
Xaa$_3$ is Glu or Asp;
Xaa$_5$ is P-Ser, P-Thr, P-homo-Ser, 4-hydroxyvaline phosphate, P-homo-Thr, P-Cys or P-Tyr
Xaa$_6$ is Leu;
Xaa$_8$ is Val or Ile;
Xaa$_9$ is Asn;
Xaa$_{10}$ is Val or Ile;
Xaa$_{13}$ is Thr;
Xaa$_{14}$ is Gly;
Xaa$_{16}$ is Leu, Phe, Tyr, or is absent;
Xaa$_{17}$ is Arg, Lys, Ala, Val, Leu, Ile or is absent; and
Xaa$_{18}$ is Arg, Lys, Ala, Val, Leu, Ile or is absent.

7. The polypeptide of claim 1, wherein the polypeptide comprises the amino acid sequence:
Pro Gly Thr Cys P-Ser Ile Cys Ala Tyr Ala Ala Cys Thr Gly Cys [SEQ ID NO: 28].

8. The polypeptide of claim 1, wherein the polypeptide comprises the amino acid sequence:
Asn Asp Asp Cys P-Ser Leu Cys Val Asn Val Ala Cys Thr Gly Cys Leu [SEQ ID NO: 29].

9. The polypeptide of claim 1, wherein the polypeptide comprises the amino acid sequence:
Asn Asp Glu Cys P-Ser Leu Cys Val Asn Val Ala Cys Thr Gly Cys Leu [SEQ ID NO: 30].

10. The polypeptide of claim 1, wherein the carboxy-terminal amino acid is selected from a D-amino acid and an L-amino acid.

11. The polypeptide of claim 1, wherein said carboxy-terminal amino acid is amidated.

12. A method for treating a gastrointestinal disorder, colon cancer, an inflammatory disorder, obesity, congestive heart failure, benign prostatic hyperplasia (BPH), pain, salt retention or fluid retention, comprising administering a composition comprising the polypeptide of claim 1.

13. The method of claim 12 wherein the gastrointestinal disorder is: a gastrointestinal motility disorder, irritable bowel syndrome, constipation predominant irritable bowel syndrome, chronic constipation, a functional gastrointestinal disorder, gastroesophageal reflux disease, duodenogastric reflux, functional heartburn, dyspepsia, functional dyspepsia, nonulcer dyspepsia, gastroparesis, chronic intestinal pseudo-obstruction, diverticulitis, or colonic pseudo-obstruction.

14. The method according to claim 13, wherein the gastrointestinal disorder is irritable bowel syndrome.

15. The method according to claim 13, wherein the gastrointestinal disorder is constipation-predominant irritable bowel syndrome.

16. The method according to claim 13, wherein the gastrointestinal disorder is chronic constipation.

17. The method according to claim 13, wherein the gastrointestinal disorder is a gastrointestinal motility disorder.

18. A method for decreasing gastrointestinal pain or visceral pain comprising administering polypeptides of claim 1.

19. A method for increasing the activity of an intestinal guanylate cyclase (GC-C) receptor comprising administering polypeptides of claim 1.

20. A pharmaceutical composition comprising polypeptides of claim 1.

21. The composition of claim 20, wherein said composition is lyophilized.

* * * * *